United States Patent
Raghavan et al.

(10) Patent No.: US 10,124,114 B2
(45) Date of Patent: Nov. 13, 2018

(54) MARGIN DETERMINATION

(75) Inventors: Raghu Raghavan, Phoenix, MD (US); Martin Brady, Baltimore, MD (US); Maria Inmaculada Rodriguez-Ponce, Munich (DE)

(73) Assignee: Brainlab AG, Munich (DE)

( * ) Notice: Subject to any disclaimer, the term of this patent is extended or adjusted under 35 U.S.C. 154(b) by 1102 days.

(21) Appl. No.: 12/423,228

(22) Filed: Apr. 14, 2009

(65) Prior Publication Data

US 2009/0270712 A1 Oct. 29, 2009

Related U.S. Application Data

(60) Provisional application No. 61/045,988, filed on Apr. 18, 2008.

(30) Foreign Application Priority Data

Apr. 14, 2008 (EP) ..................... 08103531

(51) Int. Cl.
| | |
|---|---|
| *A61B 5/05* | (2006.01) |
| *A61M 5/172* | (2006.01) |
| *A61B 90/00* | (2016.01) |
| *A61B 5/055* | (2006.01) |
| *A61M 5/142* | (2006.01) |
| *G01R 33/28* | (2006.01) |

(Continued)

(52) U.S. Cl.
CPC ............ *A61M 5/1723* (2013.01); *A61B 90/36* (2016.02); *A61B 5/055* (2013.01); *A61B 34/10* (2016.02); *A61M 2005/14292* (2013.01); *A61M 2210/0693* (2013.01); *G01R 33/281* (2013.01); *G01R 33/5608* (2013.01)

(58) Field of Classification Search
USPC ........ 600/411, 423, 427, 434, 437, 439, 466
See application file for complete search history.

(56) References Cited

U.S. PATENT DOCUMENTS

| | | | |
|---|---|---|---|
| 6,549,803 B1 * | 4/2003 | Raghavan ............... | A61M 5/14 382/128 |
| 2002/0123680 A1 * | 9/2002 | Vaillant et al. ............... | 600/407 |

(Continued)

FOREIGN PATENT DOCUMENTS

| | | |
|---|---|---|
| EP | 1 398 641 | 3/2004 |
| EP | 1 479 403 | 11/2004 |
| WO | 2006/035443 | 4/2006 |

OTHER PUBLICATIONS

"Intraparenchymal Drug Delivery via Positive-pressure Infusion: Experimental and Modeling Studies of Poroelasticity in Brian Phantom Gels", IEEE, vol. 49, No. 2, Feb. 2002).*

(Continued)

*Primary Examiner* — Michael Kahelin
*Assistant Examiner* — Shahdeep Mohammed
(74) *Attorney, Agent, or Firm* — Tucker Ellis LLP

(57) ABSTRACT

A method for identifying target regions in a tissue for local drug delivery, where functional and/or structural anatomical data such as edema and/or resection cavity is captured by an imaging system, and where the anatomical data is evaluated by segmentation techniques such as region-growing-based methods with computer assistance to determine a margin around a resection cavity and/or the volume of edema, the margin and/or the volume of edema being the target tissue for local drug delivery.

16 Claims, 15 Drawing Sheets

(51) Int. Cl.
  *G01R 33/56* (2006.01)
  *A61B 34/10* (2016.01)

(56) References Cited

U.S. PATENT DOCUMENTS

| | | | |
|---|---|---|---|
| 2002/0168618 A1* | 11/2002 | Anderson et al. | 434/262 |
| 2004/0015070 A1 | 1/2004 | Liang et al. | |
| 2006/0170679 A1* | 8/2006 | Wang et al. | 345/424 |
| 2008/0123922 A1* | 5/2008 | Gielen et al. | 382/131 |
| 2008/0183068 A1* | 7/2008 | Carls et al. | 600/411 |
| 2011/0098554 A1* | 4/2011 | Mardor et al. | 600/411 |

OTHER PUBLICATIONS

"High Flow microinfusion: tissue penetration and pharmacodynamics".*

Christopher Nikou, "A Joint Physics-Bases Statistical Deformable Model for Multimodel Brain Image Analysis", vol. 20, No. 10, Oct. 2001, pp. 1026-1037.

Sarntinoranont et al., "Computational Model of Interstitial Transport in the Spinal Cord using Diffusion Tensor Imaging", Annals of Biomedical Engineering, vol. 34, No. 8, Jul. 2006, pp. 1304-1321.

Office Action for European Application No. 08103531 dated Jul. 16, 2009.

* cited by examiner

FIG. 15a

Summary

Simulation settings

| Fluid | Duration | Selected T2 set |
|---|---|---|
| NeoPharm IL13PE38 | 96 hours | MR #3 (Axial) |

List of catheters being used for the simulation

| Name | Type | Flow rate | Total volume |
|---|---|---|---|
| Catheter 3 | Vygon 453 (2.00mm) | 4.20 µl per minute | 24.19 ml |
| Warning: Check for a suclus approx. 0.12 cm from the catheter tip | | | |

List of trajectories not being used for the simulation

| Name | Reason for not being used |
|---|---|
| Catheter 2 | Already simulated |
| Catheter 1 | Already simulated |

Press OK to start the simulation

[ OK ]  [ Cancel ]

MARGIN DETERMINATION

This application claims priority of EP 07 106 176 filed on Apr. 13, 2007 and incorporates the teachings thereof.

Disclosed is a new evaluation method, which provides further information to evaluate the parameters that impact drug distribution, especially in convection-enhanced delivery, CED.

The inventors found that there is no correlation between patient response and the compliance with catheter scoring guidelines. There is a correlation between the scoring of placement compliance with the overall targeting methods.

Coverage of Targeted Area

The goal of administering a compound locally is to cover the tissue volume that can be reasonably deemed at risk of containing tumor cells that have migrated away from the solid tumor. Thus, the first step is to define a tissue volume that will be regarded as "target tissue" for the local drug delivery.

Assuming that the highest number of migrated tumor cells per tissue volume can be found within a certain margin around the resection cavity and that the volume of edema and white matter around the resection cavity has the highest risk of recurrence, the target tissue could be defined as a predetermined e.g. 2 cm margin around the resection cavity and/or the volume of edema. For each case with available DTI data, preferably at least one of the following measurements should be performed:
  a) Overall simulation volume
  b) Overall volume of edema
  c) Volume of predefined, e.g. 2 cm tissue margin around resection cavity
  d) Volume of predefined, e.g. 2 cm tissue margin covered by overall simulation volume
  e) Volume of edema covered by overall simulation volume Air Recent studies in gels have indicated that air within the infusion system may have significant impact on the ability to achieve distribution. We also noticed air bubbles around the catheter tip, visible on the post-catheter placement CT scans. To evaluate the impact of air on the study outcome at least one of the following measurements should be performed:
  a) For each catheter: Volume of air within the infusion catheter (as visible on the CT scan).
  b) For each catheter: Volume of air outside the infusion catheter ("air bubbles")
  c) For each patient: Overall volume of air=the sum of a) and b)

PREFERRED EMBODIMENTS

Alternatively multiple distances, e.g. the 0-5 mm margin, the 5-10 mm margin, the 10-20 mm or 20-30 mm or margin and beyond can be used. The concentration curve of tumor cells vs. distance from resection cavity, which can be a logarithmic decrease in tumor cell concentration, can be considered. The T2 hyperintensity can be used as a target volume for an infusion. The location of fiber tracks can be a parameter that influences the likelihood of recurrence. If both T2 hyperintensity and distance to the resection cavity are considered, those two parameters can be combined (e.g. 0-5 mm T2 hyperintensity, 5-10 mm T2 hyperintensity, . . . ). An overlap of different areas with a certain risk of recurrence can increase the likelihood of recurrence in this overlap volume. This can be used to prioritize target volumes (e.g. priority 1=overlap of 0-5 mm margin and T2 hyperintensity and edema; priority 2=overlap of T2 hyperintesity and 0-5 mm margin, etc.), to get a more detailed picture of target coverage and survival time. If we evaluate survival time in light of the above measurements, other parameters can be considered in order to make the patients more comparable (e.g. age, KPS, bending of the catheter, general accuracy of the placement, distance of catheter to nearest sulcus, distance of catheter to any cavity, tumor sizeinfusion dose, number of catheter placed, pre-infusion edema). Imaging that can be useful to identify target areas: beyond T1-w and T2-w, others like DTI, perfusion, SPECT. Intratumoral infusion can be performed as a first step before post resection peritumoral infusion. A permeability and blood volume map can support intratumoral infusion.

Convection-enhanced delivery (CED) is the continuous injection under positive pressure of a fluid infusate containing a therapeutic agent. This technique is used to deliver drugs that would otherwise not cross the blood-brain barrier into brain parenchyma; and that would be too large to diffuse effectively over the required distances.

I. Introduction

Motivated in part by the profound difficulties associated with improving treatment of glioblastoma multiforme positive pressure infusion is considered as a means of delivering therapeutic agents into the brain. The resulting convection-enhanced flow of the agent through the interstitial space provides a means of achieving therapeutic concentrations of drugs within the parenchymal tissues on a regional basis, without the limitations imposed on delivery by the blood-brain barrier. According to an approach, one or more catheters are implanted into the brain under image-guidance, an infusion pump is connected to them to drive the flow, and the agent is then pumped directly into the target tissues which undergo dilatation in response to the pressure field and allow permeation of the agent through them (FIG. 1).

A potential advantage of the method is the ability of the agent to reach infiltrative cells that have invaded the peritumoral region and beyond, thus making it possible to significantly reduce if not halt the spread of the disease. Particularly for large molecules of the size of a globular protein of weight 50,000 Daltons and above, the diffusive spread will be often less than a millimeter in a day, provided metabolic and other loss mechanisms do not flush it from the parenchyma. The flow of a fluid co-injected with a drug can however carry such molecules far farther, and in certain scenarios fill the intervening region with a full concentration of drug per unit available volume. Diffusive spread results in exponentially decreasing concentrations away from a source.

Following CED of novel therapeutic agents in humans with malignant gliomas, we have been able to obtain images that document the spatial distribution of large molecules in several patients with brain tumors. These data demonstrate that CED is capable of significantly enhancing the spatial distribution of drugs beyond that which would be obtained by diffusion alone. We see that an important issue associated with the development of convection-enhanced delivery (CED) is that of understanding how the spread of the infusate within the brain might deviate from an ideally-sought volume of distribution. In the next section, we provide an overview of the various factors affecting the spread of infused volume. This naturally leads into how we mitigate the deleterious effects of some of the phenomena and we discuss some aspects of the delivery catheters in the following section

II. Factors Affecting Drug Distribution by CED

In most procedures for intraparenchymal infusion or injection, the delivery device is stereotactically guided to its intra-cranial target through a burr hole. For slow infusion processes, typically in humans of rather less than 0.3 milliliters per hour, the catheter might be left indwelling for several days. Conventional MR/CT imaging studies are typically used pre-operatively to estimate the optimal insertion trajectory. However, the final operative details of the implantation procedure can be specific to the design of the delivery device, the rate at which the infusion or injection is to occur, and the number of devices that must be inserted and/or passes that must be made to obtain adequate therapeutic coverage of the targeted volume. Infusion methodologies for both framed and frameless stereotaxis have been developed, with forms of the latter optimized for use in the interventional MR setting.

The key features that affect the distribution of molecular solutions when pumped into brain parenchyma are summarized in FIG. 2.

Once the pump parameters, as e.g. the flow rate and duration, have been set, the fluid flow in the poroelastic medium of brain parenchyma is the primary carrier of large molecule drugs. The interstitial pathways in the brain allow such convective transport independent of the size of the molecule, for a range of sizes. Of course, factors such as lipophilicity can affect the transport, but for water soluble proteins, convective transport dominates at least for short times. The flow of fluid in the brain is quite tortuous, and the convective transport of the drug is limited by various barriers including the pial surfaces of the cortex. Over longer times, the processes of diffusion, of loss through the capillaries, and of course drug action (metabolism) determine the distribution patterns of the drug. These processes are sketched in FIG. 3. However, before these fundamental mechanisms of transport and of metabolic action take place, there are several issues that should be dealt with: tissue damage upon catheter insertion, the ever-present air bubbles that, if not properly treated, can provide unpredictable paths for following fluid flow, and so on. We have listed the factors in the table below, which we describe following from there (Table 1).

TABLE 1

Phenomena relevant to CED and their determining parameters

| Phenomenon | Determining parameters |
|---|---|
| Tissue damage on catheter insertion | Obviate by catheter design and insertion procedure |
| Air bubbles | Obviate by stylet and catheter design, and insertion protocol |
| Backflow along catheter walls | Poroelastic parameters near catheter: elastic moduli extracellular volume hydraulic conductivity of tissue |
| Fluid flow in extracellular brain tissue | hydraulic conductivity of tissue Also induced variation of excess pressure |
| Efflux rate of water from brain tissue | Capillary hydraulic conductivity |
| Drug transport | Diffusion tensor of drug Convective velocity |
| Drug efflux from tissue | Capillary molecular permeability - area product |
| Drug metabolism, binding, and other effects | |

II.1 Tissue Damage, Reflux, Etc.

One phenomena during infusion is backflow of the infusate along the insertion track of the catheter. This can happen for one of two reasons. First, and most obvious, backflow can occur if the catheter has mechanically disrupted the tissue enough to allow a void to form around its outer wall. In this case, the infusate simply refluxes through that gap with relatively little pressure-driven flow into the target tissues. It seems obvious, that soft catheters are less likely to cause mechanical disruption. In particular, surgeons routinely view brain shifts during craniotomies that requires them to mentally adjust the image-guidance system for proper positioning of catheters during post-operative infusions. Soft catheters can move with the brain shift and cause less disruption and breaking of seals, thereby preventing this form of backflow. The more intrinsic reason for backflow is next described.

II.2 Transient and Steady-State Characteristics: Intrinsic Backflow

Even when no void has been formed during insertion or if the tissue has sealed against the outer wall, a second type of backflow can occur. In it, the pressure associated with the infusion process pushes against the tissues and causes them to separate minutely from the catheter, until such point as the shear forces in the tissue balances the pressure field and the retrograde axial flow stops. This latter type of backflow, intrinsic backflow, is the kind illustrated in FIG. 4.

The predictions or theories of backflow have been based on steady-state considerations and depend on the assumption that the backflow is fully developed before the fluid has spread significantly into tissue. The basic mathematics of poroelasticity reveals that the pressure is diffusive and thus does not reach a constant value in a finite time. Thus the experimental conditions under which the backflow predictions can be validated are special. They require relatively small diameter catheters and either strong resistance to spread in the tissue, or ease with which the tissue can be deformed by fluid pressure, or both. Nevertheless, a central fact remains: namely, that backflow can occur and allows the fluid to flow back along the catheter track for several centimeters, and this must be accounted for. Such backflow can result in spread of the agent into regions of the brain where it is not intended and, possibly, in diminution of the dose otherwise needed within the target tissues. The same holds for reflux during withdrawal. The problem could be particularly acute in cortical infusions, where backflow of the agent along the insertion track and into the subarachnoid space could occur, with subsequent widespread distribution of the agent by the circulating cerebrospinal fluid. A model of the mechanics of the backflow process indicates that the backflow distance (for a fixed rate of fluid delivery through the catheter) varies as the four-fifths power of the catheter radius. In testing this model versus observations of infusions predicted backflow distances on the order of 20 mm were found to indeed occur. As a result, for infusions into humans, the best navigations systems offer the following guidelines:

1. Depth Line, which displays a cylinder along the catheter trajectory representing a recommended zone within which the catheter should not cross any pial surfaces. This line must be computed dynamically based on at least flow rate and catheter size. Further the depth line should show a sphere around the catheter tip representing a recommended distance to fluid filled cavities.
2. Distance Line, which displays a sphere of 2 cm diameter around the catheter tip representing the recommended minimal distance between catheters.

The outer circle gives the Distance Line and the inner circle in combination with the cylinder along the trajectory the Depth line (FIG. 5).

FIG. 6 illustrates the leakage of infusate into the subarachnoid space via backflow up the catheter in an actual infusion. A 0.85 mm diameter catheter was inserted through a burr hole into in-vivo pig brain to a depth of 14 mm from the cortical surface. 1:200 Gd-DTPA:water solution was infused at 5 microliters per minute. 3D MR imaging (3D-FSPGR, TR=7.8 ms, TE=3.2 ms, 256×256 matrix, FoV=20 cm, 1 mm slice thickness, 60 slices, 2 NEX, flip angle 15°) was performed to analyze the dispersion of the Gadolinium marker. Images taken after 32 minutes of infusion show evidence that the infusate has mostly leaked into the subarachnoid space, distributing widely along the contours of the cortex, while little distribution into the white matter was recorded.

II. 3 Air Bubbles

Dissolved air and air bubbles are important factors in affecting the reproducibility and predictability of the delivery.

II. 4 White Matter Edema

So far, we have focused on situations where the backflow or flow into fluid filled cavities would almost totally compromise the infusion. There is, however, another path which very significantly affects infusions, and which needs to be considered. This is the increased fluid permeability offered by the white matter tracts, and which increases in edematous brain. However, just infusing fluid into white matter produces changes that appear very similar to vasogenic edema. When infusing into white matter that does not already contain edema, edema appears around the catheter (see FIG. 7).

As can be seen in the figure, relatively little edema is seen near the tumor recurrence which is below the resection cavity before infusion. After 44 hours of infusion, a large and intense edema surrounds the catheter. The extent of the edema appears to match the extent of the infused fluid closely, according to infused gadolinium and SPECT markers. The level of the infusion-related edema for a 4.5 μL/min infusion is often greater than that observed of tumor-induced vasogenic edema. In T2-weighted images, the T2 levels near the infusion reach values very near that of fluid-filled cavities and ventricles. The infusate itself may have a higher T2 than that of cerebro-spinal fluid (CSF), so it may be difficult to make a quantitative assessment from the T2 weighted values as to whether the infusion-induced edema has a water fraction higher than that of the average vasogenic edema.

II. 5 Target Heterogeneity

In describing the strong effects of edema in white matter upon the distribution of the infusate, we have already touched upon the inhomogeneity of the tissue, though this is one induced by the infusion. However, even in its initial state, the resistance to fluid flow in brain tissue is both anisotropic (dependent on the direction of the flow) and heterogeneous (dependent on location within the brain). These two aspects are illustrated in FIG. 8, which involves both some imaging and some mathematical developments. For the moment, the FIG. 8 (b) may be taken to be direct representations of the degree of inhomogeneity (variations with location in tissue of some average of the values of hydraulic conductivity along its principal axes) or of the anisotropy (a measure of the ratio of the largest and smallest of the values along the principal axes). The brightness of the image is a direct map of these quantities.

II. 5 Active Tumors and BBB Disruption

Active tumors present a variety of additional barriers to drug delivery including: high interstitial tumor pressure; decreased vascular surface area with a markedly more heterogeneous distribution of blood vessels than the case for normal cells; increased intra-capillary distances; and peritumoral edema. Most of these originate with a disrupted BBB.

iii. Delivery Devices: Catheters

We now discuss some aspects of the delivery devices, and especially catheters used for CED. Early on, the catheters used for intraparenchymal delivery (the only mode of delivery we discuss) were multiport catheters originally devised for ventricular shunts e.g., for hydrocephalus. An example of one of the delivery devices used to date was the catheter employed in the Phase II Clinical Trial of HN-66000, a diphtheria toxin conjugate developed at the NIH. Two PS Medical CSF Cardiac/Peritoneal catheters (Medtronic PS Medical, Goleta, Calif.), 2.1 mm OD and 1.2 mm ID, were stereotactically inserted such that the distal ends were spaced approximately 1 cm apart. The difficulty with this approach is one of obtaining predictable and adequate flows from all of the catheter's ports, frequently the flow is out of the most proximal port. This can make it difficult to control the flow from a linear sequence of ports placed along the catheter axis, unless the pressure field inside the catheter is hydrostatic. That is unlikely since most of the impedance to the infusion flows occurs in the tissues themselves, and there is typically a small but non-negligible gap between the outer wall of the catheter and the parenchymal tissues which serves as a sink for the pressure field. An example of this phenomenon is shown in FIG. 10, where the distribution of dye from an eight-port ventricular catheter inserted into gel reveals that there is flow only from the proximal ports. FIG. 10 shows an infusion of bromophenol blue dye through an eight-port ventricular catheter placed in gel. The dye infuses through the most proximal ports only, with no distribution of it through almost all of the other ports. Virtually all of the pressure drop occurs across only the most proximal port, even for the case of an essentially hydrostatic pressure field inside the catheter. The same phenomenon has been observed during clinical infusions.

Motivated by these deficiencies, we tested several different designs to evaluate the volumes of distribution and pressure profiles. The devices studied are shown in FIG. 11. The in-vitro test procedures and other details are in which may be consulted for details of the results, and images of the infusions.

Parenthetically, we may remark that the great advantage of this type of in vitro study is the relative speed with which the exploratory infusions can be carried out, and the very low cost of doing such experiments (the agarose gel costs only pennies per sample, in contrast to the vivarium expenses that can accumulate for in vivo testing). While in vivo testing of medical devices like these is an unavoidable necessity prior to ultimately using them in human clinical trials, a substantial fraction of the expenses can nevertheless be avoided by following the gel-based route.

The physical characteristics of the catheters are listed in Table 2, including the configuration of port holes and material.

TABLE 2

Characteristics of catheters evaluaed in-vitro.

| Catheter | Outer Diameter | Inner Diameter | Material | Ports |
|---|---|---|---|---|
| A | 0.95 mm | 0.75 mm | rigid polyamide | single, end |
| B | 2.5 mm | 1.25 mm | flexible silicone | single, end |
| C | 2.5 mm | 1.25 mm | flexible silicone | single, laser cut end |
| D | 2.25 mm | 1.0 mm | flexible silicone | four, radial slits |
| E | 1.75 mm | 0.75 mm | clear silicone | 3 radial lines of 10 laser cut holes |
| F | 2.0 mm | 1.0 mm | barium-impregnated silicone | single, end |
| G | 2.25 mm | 0.75 mm | silicone | fishmouth |

Representative data showing the volumes of distribution and pressure profiles found for each catheter are shown in FIGS. 12 and 13. The dye infused into the 0.6% gel was bromophenol blue (MW=690), the flow rate was 5 microliters per minute, and the pressure is measured in mm Hg. Photos were taken at 10 minutes following the start of the infusion and at 40 minutes, when the run was ended.

Of course, there are several possible solutions to this problem with multiport catheters. One is to significantly increase the resistance within the catheter by introducing porous material. This high resistance equalizes removes the sensitivity of the flow to individual pressure drops across the ports and allows all ports to allow fluid flow. Another solution to this problem is to have several separate lumens within one catheter body, with each lumen feeding its own port hole. This ensures that there will be adequate flow from each port hole, and in fact allows for separate adjustment of each flow rate and/or the simultaneous infusion of different agents into the targeted tissues. A logical extension of any of these concepts is that of introducing a catheter with controllable port holes. Indeed, specialized injection cannulas with multiple side ports and co-axial lumens have also been used in human trials of cell delivery, and withdrawn in time sequences that allow the surrounding tissue to hold the implant in place during removal of the cannula from the brain, thus circumventing the reflux problem.

However, the simplest solution is to use catheters with a single end port. Catheters currently used for infusion are substantially larger than the very thin cannulae which have been characterized as optimal in rodent brain. Nevertheless, the larger scale of human brain and allowance of time after placement of the infusion catheters is expected to allow some backflow along the catheter tract while maintaining good distribution of the infusate.

IV. Modeling

In Section II, we described several of the important determinants of the flow of infusate injected continuously into the brain. The equations that describe such flow in the idealized situation of a small spherical source, and isotropic, homogeneous tissue were analyzed in Morrison P F, Laske D W, Bobo H, et al: High-flow microinfusion: tissue penetration and pharmacodynamics. Am J Physiol 266: R292-R305, 1994. In Table 3, we display the parameters that are computed from the imaging, while the following table shows the validation studies for intermediate variables in the computation itself, not directly derived from image processing. We first review the principal imaging methods we currently employ and which parameters we expect to obtain from these. More detailed discussion of how these parameters are obtained follow.

TABLE 3

Parameter

K (tissue hydraulic conductivity)
$l_2$ pore fraction)?resting???
$k_{irr}$ (irreversible loss of drug from tissue)
$D_M$ (diffusion tensor of drug molecule)
$L_p s$ (capillary hydraulic permeability -density product)
(effective elastic constants of l?? tissue)

Diffusion Tensor Imaging

MR diffusion tensor imaging, with suitable image post-processing, reveals the self-diffusion tensor, D, coefficients of water in brain tissue, using well-known techniques, such as described by Basser in 1994. After suitable filtering and correction for motion and distortion, average diffusion coefficients (ADCs) are computed for at least six independent gradient directions. A linear system of equations is then solved using these ADC values to obtain the six coefficients of the water self-diffusion tensor at each sample point. Furthermore, cross-property relations between diffusion and other transport processes can be employed to estimate seemingly unrelated parameters from the diffusion tensor coefficients. This method has been used recently to estimate the electrical conductivity tensor, as described by Tuch in 2001.

One key to be able to utilize the diffusion tensor data is to be able to extract the extracellular diffusion tensor. By this we mean essentially the thought-experiment of zeroing out the contribution of any intracellular water, and of any exchange (loss of extracellular water to the intracellular compartment, in this case). Roughly speaking, building upon the relatively complete model of the MR signal under diffusion-weighted imaging protocols, we choose gradient strengths so that the signal is biexponential to an excellent approximation, with the exchange contribution to the signal being negligible. We then obtain just the extracellular component by comparing normalized signals at two such gradient strengths. For this to work, the diffusion times must be relatively short. We have developed this technique in order to obtain the hydraulic conductivity tensor, which is key to any simulation involving convective transport. There are three sets of parameters that we currently estimate from DTI.

Tissue hydraulic conductivity K: The essential idea used in inferring K is that the anisotropies of the diffusion tensor give us geometric information about the medium, which we can then use in inferring the hydraulic conductivity. This expansion can be used for the diffusion tensor of water which is known from MRI, and the probability functions inferred then in at least a least-squares sense. These estimated probabilities can then be plugged into the expansion now of the hydraulic conductivity which can then be obtained. This can be done at several levels of approximation which are developed in internal reports. Furthermore, there are several other expressions for transport coefficients. Pore fraction φ: The dependence of the principal eigenvalues of the diffusion tensor as a function of φ can be estimated for different anisotropies (mainly when the anisotropy is very strong, or when it is isotropic) from theory. We can then fit this to the measured values for a fixed anisotropy in different parts of the brain tissue which will then allow us to infer ratios of pore fractions. The absolute pore fraction is then estimated from some reliable baseline value in grey matter.

Diffusion tensor for molecules, $D_{\{e\}}$, diffusing within the extracellular fluid: $D_{\{e\}}$ can be inferred in exactly the same fashion as K. Namely, the cluster expansion of is used to develop D_{M} in terms of the point probability functions already obtained from the DTI. Ideally, we should know the value of the molecular diffusion coefficient in water from other sources. However, if we do not have ready access to that, we scale this value according to the size of the molecule. Future developments can include obtaining the diffusion in saline solution as a baseline value, which allows the parameter estimation from DTI to proceed with more confidence, or enhancing the theory-based scaling to allow for the shape of the molecule, and its interactions with the local environment, or both.

The diffusion tensor field can also be used to identify fiber tract pathways, by examining the anistropy of the tensor and the direction of the major eigenvector.

Dynamic Contrast Enhancement Imaging

Dynamic contrast enhancement imaging provides quantitative methods for obtaining several physical parameters of importance in tumorous tissue by following changes in signal intensity from tracer molecules injected into the bloodstream. This imaging modality follows the movement of tracer concentrations from through the blood vessels into tissue (and, if the measurements are carried out for long enough, back again into vessles), primarily in regions of significant disruption of the blood-brain barrier. In particular, the permeability-surface area product of the capillaries, local blood flow and blood volume can be estimated via image post-processing using various models of tracer transport. This data is essential for simulations of transport near tumor tissue. The permeability-surface area product, however, is specific to the tracer molecule used. By varying the size of the tracer element used, we develop methods for estimating the permeability of larger molecules. This will make the assumption, for example, that albumin, suitably attached with a marker such as Gadolinium, will behave in its movement across the blood-brain barrier (BBB) in essentially the same way as a similar-sized therapeutic molecule, e.g., IL—13 (both are hydrophilic and have molecular weights close to one another, around 60,000 Daltons).

V. Tracking Infusates

The final result of any model of infusion is of course the distribution of the particle in question, whether it be a large molecule protein therapy, a viral carrier of gene therapy, a cell, or other particulate. In order to validate such a model, one should be able to measure agent concentration in tissue. Leaving aside immuno-histochemistry which involves sacrifice of an animal, we briefly discuss in-vivo measurements of concentration of molecules and other particles.

There is a great advantage to use human in-vivo imaging of infusate distributions since it opens the door to active feedback control of delivery in real time. There have been published results reporting of the adequacy of T2-weighted images to track infusate distribution based on the drug effects on the tissue It was also reported about the enhancement of T2 signal as a consequence of fluid administration by CED methods. Experiments with nonhuman primates where Gd-chelate was co-injected to monitor drug distribution have also been investigated. New markers for MRI can be developed: however, Gd-chelates form excellent MR markers. We also briefly mention magnetodendrimers. These chelates can be bound or conjugated with ease to various proteins, including therapeutic proteins, and therefore offer direct visualization of a proposed drug. Gd is a marker that works by its effects on surrounding water molecules, and hence is required to be in relatively large concentrations to be visible The use of Gd-chelate is a very appropriate surrogate marker to track fluid distribution. A physician can handle with the combination of all possible images (e.g. T2-w and SPECT) to track infusate distribution and specially also track along time (during treatment and after).

FIGURES

FIG. 1: Schematic of a convection-driven infusion. (b), T2w MR image of an infusion of a cytotoxin into human brain. The white enhancement around the catheter (green line) depicts the spread of the infusate after 96 hours of continuous pressure-driven infusion.

FIG. 7: (a), T2w MR image acquired before the start of an infusion using two catheters (not shown). (b), same image slice 96 hours into the infusion shows increased T2 enhancement caused by the infusate. The added volume leads to an elastic deformation of the brain as visible by a slight midline shift and a shift of the resection cavity margins.

FIG. 8: (a), slice of a map of the trace of the hydraulic conductivity tensor, computed from diffusion tensor MR images. Bright areas show regions with high conductivity. (b), slice of a map of the anisotropy of the hydraulic conductivity tensor. Bright areas show regions with high directionality (anisotropy) of the hydraulic conductivity.

FIG. 9: (a), schematic diagram of the pressure differential between the extratumoral interstitial pressure and the intratumoral interstitial pressure. (b), contrast enhanced T1w MR image showing a tumor in a dog brain with a catheter placed through the tumor with the tip about 1 cm beyond the tumor mass inside adjacent tissue. (c), T1w MR image showing the same slice as in (b) with Gd DTPA infused through the catheter. The image reveals that the fluid does not enter the tumor mass but rather distributes around the border of the tumor.

Abbreviations used: CED, convection-enhanced delivery; CI, confidence interval; CSF, cerebrospinal fluid; DTI, diffusion tensor imaging; HSA, human serum albumin; MG, malignant glioma; SIM, simulation; SPECT, single photon emission tomography; Vd, volume of distribution Convection-enhanced delivery (CED) is a drug delivery technique that uses a positive infusion pressure to deliver therapeutic agents directly into the interstitial spaces of the brain. Target tissue anatomy and patient-specific physiology play a major role in drug distribution using this technique. MR diffusion tensor imaging is used to predict patient-specific drug distributions by CED.

Malignant gliomas (MGs) remain rapidly and almost uniformly fatal. Systemic delivery of many potentially effective drugs to these and other intracerebral tumors is hampered by the restrictive blood-brain barrier and high intratumoral pressure. The innovative intracerebral drug infusion technique of convection-enhanced delivery (CED) uses a positive infusion pressure to deliver therapeutic molecules throughout the interstitial space of brain parenchyma theoretically resulting in homogeneous distribution of macromolecular therapeutic constructs at clinically relevant volumes and concentrations. CED is capable of producing extensive and relatively homogeneous distribution of a substance or drug, such as 123I-labeled albumin in the brains of patients with MGs. However, spatial distributions could vary significantly from patient to patient. Furthermore, the actual geometry of the distribution in a given patient is not obviously predictable.

Based on theoretical considerations and analysis of preliminary images, interpatient variability can be explained by disparities in the physiology and anatomy of different brain tissue regions. Although these disparities cannot be fully appreciated with conventional anatomic MR images, mathematical models suggest that diffusion tensor imaging (DTI) can provide much of the necessary information.

Guidelines for catheter insertion can be as follows:
1. Catheters should enter through separate cortical surface sites if possible and be at least 3 cm from the surface to minimize backflow.
2. Catheter tip located 2-3 cm from the margin of resection or planned resection.
3. Catheters must not enter the ventricle and be at least 1 cm from the ependymal surface.

Others overall target selection criteria are:
a. Catheters should be placed well into the contrast-enhancing tumor (pre-resection catheter placement) or peritumoral brain parenchyma (pre-resection or post-resection).
b. Catheters should be positioned at least 2-4 cm apart and placed preferentially adjacent to any region(s) of known or suspected residual solid or infiltrating tumor as determined by the neurosurgeon.
c. To the extent possible, catheters will be located in the primary anticipated direction of spread along white matter tracts, as defined by pre-operative T2 abnormalities or anatomic information, and at opposite 'poles' of the tumor or resection site.

Guidelines (1)-(3) are the relevant to prevent leakage, the most serious phenomenon affecting drug distribution.

Imaging Parameters

Brain MR imaging with unenhanced and contrast enhanced T1-weighted (e.g. TR=22, TE=7), T2-weighted (e.g. TR=6200; TE=123), and DTI (e.g. 6 direction 3 mm thick contiguous slices, b value=1000; TR=8800; TE=80) is obtained before each catheter placement to provide input data for the simulation algorithm. MR scans are obtained on a 3T scanner (e.g. Siemens Medical Systems; Erlangen, Germany). SPECT (single photon emission tomography) scans with a three head scanner (e.g. Trionix Research Labs, Twinsburg, Ohio, U.S.A.) fitted with two TRIAD LESR fanbeam collimators and a precise pinhole collimator are then obtained later, e.g. 24 and 48 hours after infusion initiation to evaluate the distribution of an infused substance. The volume of distribution (Vd) is subsequently determined by a threshold pixel method for calculating the volume of small spheres ranging in size from e.g. 1.3 cc to 5.3 cc in a brain phantom model. The Vd is based on the volume depicted by the SPECT at a fraction, e.g. 50% of the maximal signal value.

Sulcus-Detection Algorithm

Before simulating the actual fluid distribution, the surgical planning software first delineates fluid-filled surfaces, such as sulci, resection cavities, and ependymal surfaces using a T2-weighted MRI dataset because the resolution of clinically obtainable DTI datasets is currently too low to define these small anatomic structures. This is done using a three-dimensional ridge filtering method. The ridge filtering method is based on a local second-derivative operator that is maximized at thin peaks in the T2-weighted input image. This filter is effective at locating most sulci (if they are visible in the underlying image). However, other sharp boundaries, as may be found in areas of significant edema, can confound the algorithm. To prevent misclassifications that may result in these areas, the workflow can be modified to include a pre-emptive step consisting of the manual segmentation of the edematous brain areas. To detect cavities and sulci, the pore fraction computed from the MR DTI scan can also be used. It is assumed that cavities exist where the pore fraction is estimated to be close to one. This methods are jointly referred to as "sulcus detection".

When running the sulcus detection algorithm, the software first uses the infusion flow rate and catheter dimensions to estimate the length of fluid backflow along the catheter track. Within this estimated length, the software then checks each catheter trajectory for the presence of a segmented surface or cavity. If a surface is detected, the software brings up a dialogue box containing a warning regarding a potentially poor catheter trajectory which is at risk for failing to produce intraparenchymal distribution of the infusate. This allows the user to go back to the planning mode and check the catheter trajectory for potential re-positioning (FIG. 20A). Only after the user accepts the trajectories at this stage, is the actual simulation of fluid distribution performed as described below.

Simulation Algorithm

Morrison et al. (Morrison et al., 1994) describes the rate of change of drug concentration per unit tissue volume "c" as a approximation from a sum of diffusion, changes due to convection, and losses:

$$\frac{\partial c}{\partial t} = \nabla \cdot (D \cdot \nabla c) - \nabla \cdot (vc) - \frac{k}{\phi} c \qquad \text{Equation A1}$$

In this equation, "D" stands for the diffusion tensor of the drug molecule in the interstitial space, "v" describes the velocity of the interstitial fluid, "φ" □ is the pore or interstitial volume fraction, and "k" accounts for the irreversible metabolism losses and for the disappearance through capillaries. Reference is made to U.S. Pat. No. 6,549,803 and U.S. Pat. No. 6,464,662). The equation is solved with appropriate boundary conditions for an individual brain obtaining and estimating the parameters (D, v, φ□□k) from MRI and from the literature.

The velocity in the interstitial space is computed applying D'Arcy's law which relates the interstitial pressure gradient and the interstitial fluid velocity linearly, the coefficient being the hydraulic conductivity tensor, "K":

$$v = -K \cdot \nabla p \qquad \text{Equation A2}$$

Finally, by combining Equation A2 with an expression for the differential conservation of water, the following equation is obtained:

$$\nabla \cdot (\phi K \cdot \nabla p) = L_p sp \qquad \text{Equation A3}$$

where Lp is the capillary hydraulic conductivity governing the rate of net flow of water across capillary membranes and s is the capillary area per unit tissue.

The main parameters, D, K, and φ are computed from MR imaging. The water self-diffusion tensor field, Dw is obtained from MR-DTI. From this, the diffusion of the drug molecule is estimated based on a simple scaling law based upon the weight of the molecule. Dw is also used to estimate the porosity, φ, and finally a map of the hydraulic conductivity tensor, K, is obtained from Dw and φ via cross-property relations. We thus obtain patient-specific three-dimensional maps of these quantities, which are used as input for the computer simulation algorithm.

The simulation begins by solving Equation A3 for the pressure field related to the infusion. The required boundary condition in this partial differential equation for the pressure is obtained by computing the pressure profile along the catheter shaft based on a poroelastic model of backflow. Given the pressure along the catheter shaft, Equation A3 is solved and then the fluid velocity field v is obtained using Equation A2. Finally, using this estimate for v, Equation A1 is solved. The result is thus a patient specific map of fluid concentration at any desired time point during or after the infusion. In surgical planning software (Therataxis, Baltimore, USA and BrainLAB AG, Munich, Germany), this result can then be displayed as a three-dimensional overlay on the anatomical MRI scans, allowing the physician to assess whether the volume covered with the infusion given a set of catheter trajectories will be satisfactory or not. The software assists in the optimization of the planned trajectories by allowing the simulation to be run at different catheter locations. The simulation algorithm is not currently designed to handle the effects of large local variations in blood-brain-barrier permeability which may be seen within unresected tumor tissue, although we believe that by incorporation of dynamic imaging of contrast enhancement this may be possible. Evaluation of the simulation algorithm was, therefore, only performed on catheters placed in the post-resection setting.

Evaluations

Trajectory Assessment

For all catheters trajectories evaluated, the sulcus detection algorithm was run first. For all trajectories that were not identified as problematic by this algorithm, the fluid distribution simulation was performed.

Volume Match and In-Plane Distance Deviations

The accuracy of the simulation in predicting the Vd was evaluated by dividing the volume concordant between the simulation (SIM) and the SPECT by the sum of all volumes:

$$\text{Volume Match} = \frac{\text{Concordant Volume}}{\text{Concordant Volume} + (SPECT > SIM) + (SPECT < SIM)}$$

whereby (SPECT>SIM) stands for the volume where the SPECT signal outline was larger than the simulation signal outline, and (SPECT<SIM) describes the SPECT signal that was not covered by the simulation (FIG. 20B).

The accuracy of the simulation in predicting the geometric distribution of the infusate was evaluated by measuring the maximum distance between the windowed SPECT border and the simulation border at the 50% isodose level was measured. For this measurement, the slice with the largest distance between the simulation and the SPECT signal was always used (FIG. 20C).

Clinical Utility

The purpose of the simulation software is to support clinicians in identifying catheter trajectories unlikely to provide drug deliver to the desired anatomic distribution, and for suitable trajectories, to estimate the expected volume and geometric distribution of the tissue covered by the infusate. Thus, for each infusion catheter evaluated, the software was graded as "clinically useful" if it identified catheter trajectories that failed to deliver any drug into the desired anatomic region or if it provided a fluid flow simulation with volume match of >50% or an in-plane deviation of <10 mm.

MR-DTI images contain valuable patient-specific information that could be effectively exploited to assist in the optimal placement of intracerebral catheters for CED. A pilot software algorithm, that incorporates patient-specific data derived from MR-DTI, can provide clinically useful information regarding the location, volume, and geometry of distribution of a radiolabeled imaging tracer delivered by the novel technique of CED in patients with MG.

FIGURE LEGENDS

Figure 1:
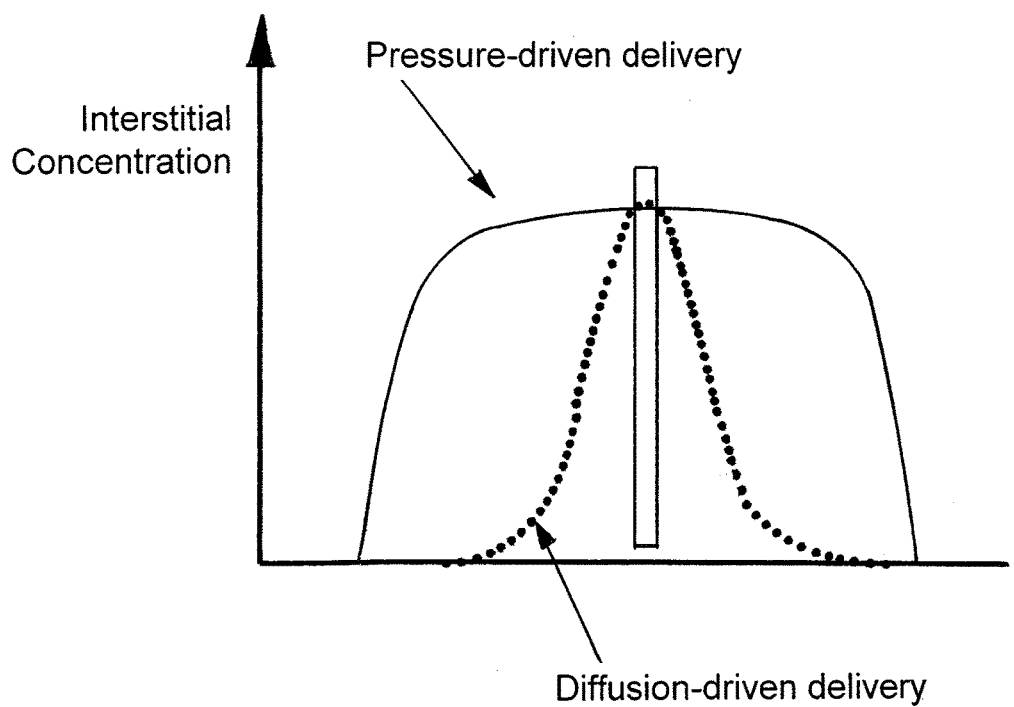
FIG. 1 is a schematic showing concentration profiles for pressure-driven and diffusion-driven deliveries. Compared with diffusion-driven delivery, the pressure-driven delivery results in a higher concentration extending farther from the delivery site.
Figure 2:
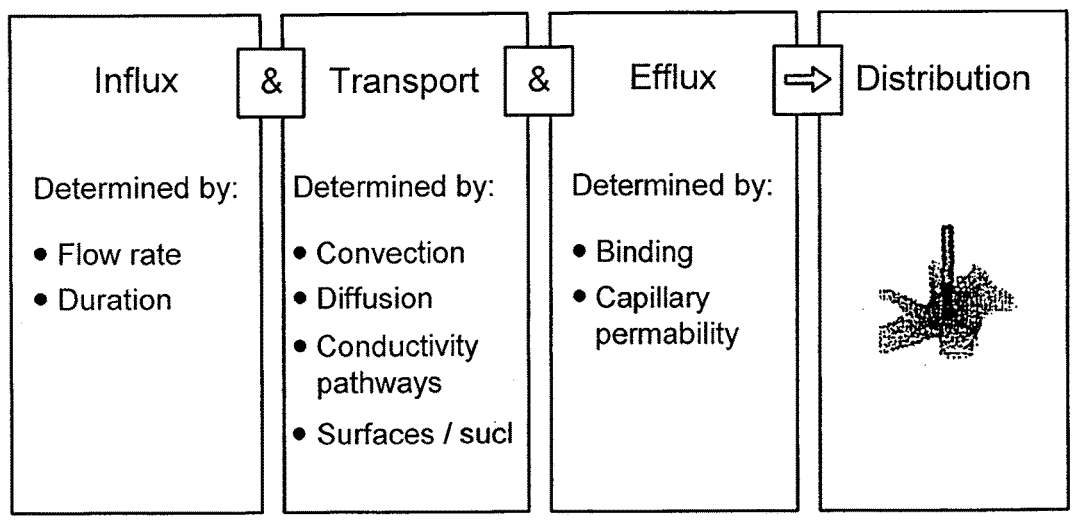
FIG. 2 is a diagram depicting a possible subdivision of the problem involved in CED. The distribution can be inferred from knowledge about influx, transport, and efflux parameters.
Figure 3:
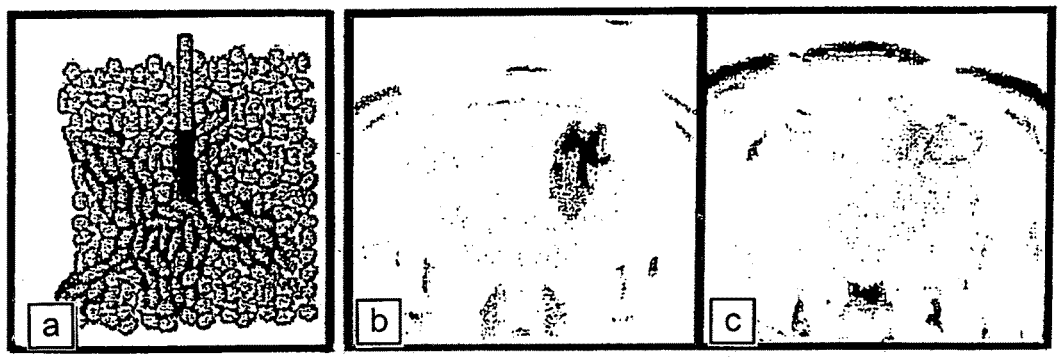

FIG. 3a is a sketch illustrating an infusion catheter in tissue (not to scale). Orange elongated cells represent white matter tracts. The fluid infused from the catheter forms a small annulus around the outside of the catheter, the backflow. This cylinder is the source of the subsequent infusion, which preferentially follows the white matter tracts.

FIG. 3b is a $T_1$, -weighted MR image demonstrating the infusion of Gd-DTPA into a pig brain. The infusion pattern has an irregular shape, preferentially following the white matter tracts. The image was acquired at the end of the infusion.

FIG. 3c is a $T_1$ weighted MR image obtained 1 day after the infusion was finished, depicting the effects from the same infusion shown in panel b. The Gd-DTPA has diffused to distances far beyond the original volume shown in panel b.

Figure 4:
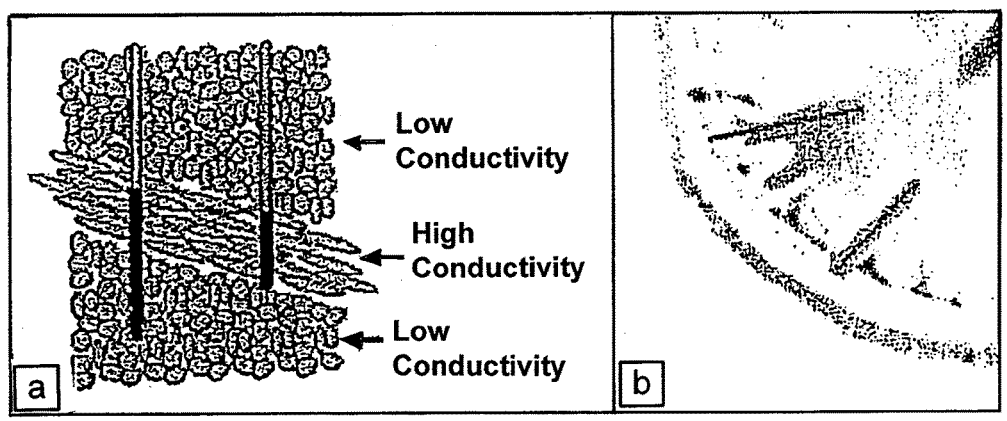

FIG. 4a is a schematic drawing depicting two infusion catheters in inhomogeneous tissue (not to scale). The backflow distances, represented by dark blue cylinders around the catheter tips, vary depending on the hydraulic conductivity of the adjacent tissue. The backflow length is extended in areas of low conductivity.

FIG. 4b is an overlaid $T_2$-weighted MR image demonstrating backflow distances (green areas) simulated for two different catheter trajectories (yellow lines). The simulated backflow distances vary significantly within a patient, depending on the chosen trajectory.

Figure 5:
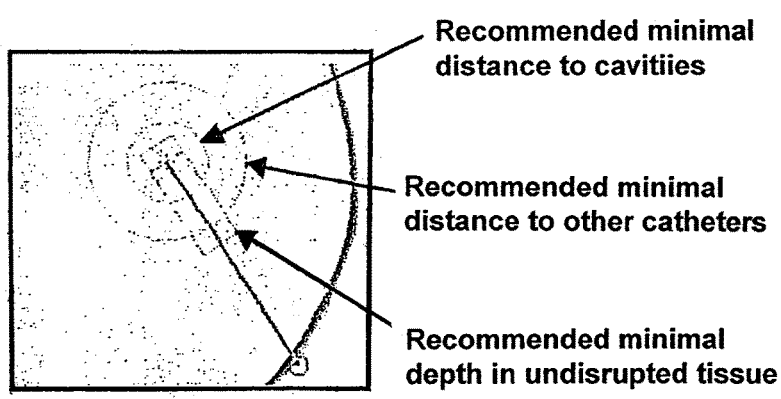
Figure 6:
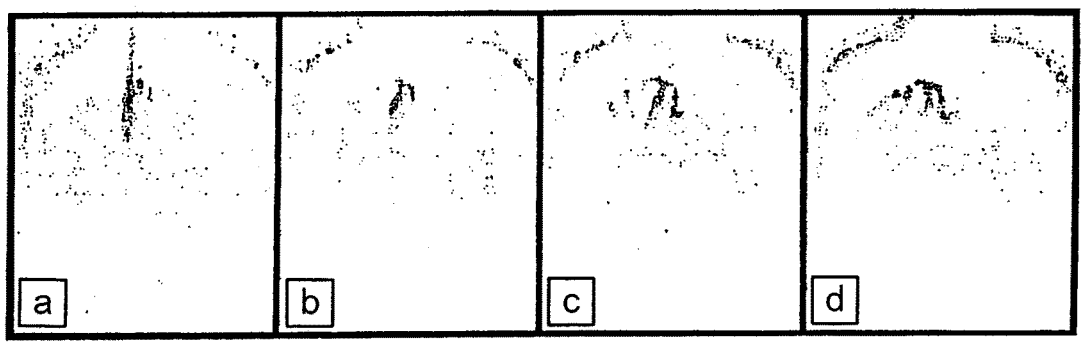

FIG. 5 is a $T_1$-weighted MR image demonstrating the planned catheter trajectory (bold green line). The thin lines around the planned trajectory represent guidelines designed to indicate the suitability of the trajectory in providing an infusion within the interstitial space.

FIGS. 6a-6d are four $T_1$-weighted three-dimensional spoiled gradient-recalled acquisition MR images showing the effects of an infusion of a Gd-DTPA and water solution (1:200). The slice thickness is 3 mm with no gap. The infusion catheter is visible in the first slice (a). The images reveal leakage and spread of the infused agent into the subarachnoid space.

Figure 7:
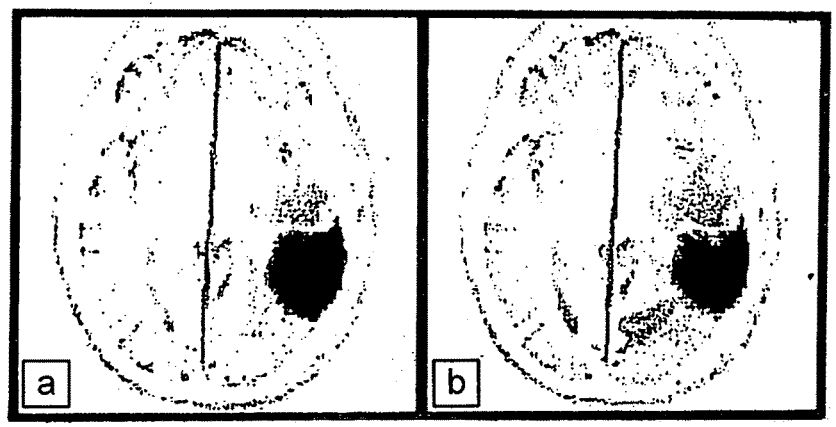

FIG. 7a is a $T_2$-weighted MR image acquired before the start of an infusion with two catheters.

FIG. 7b is a $T_2$-weighted image of the same slice 96 hours into the infusion showing increased enhancement caused by the infused agent. The added volume leads to an elastic deformation of the brain, which is apparent by a slight mid-line shift and a shift of the resection cavity margins.

Figure 8:
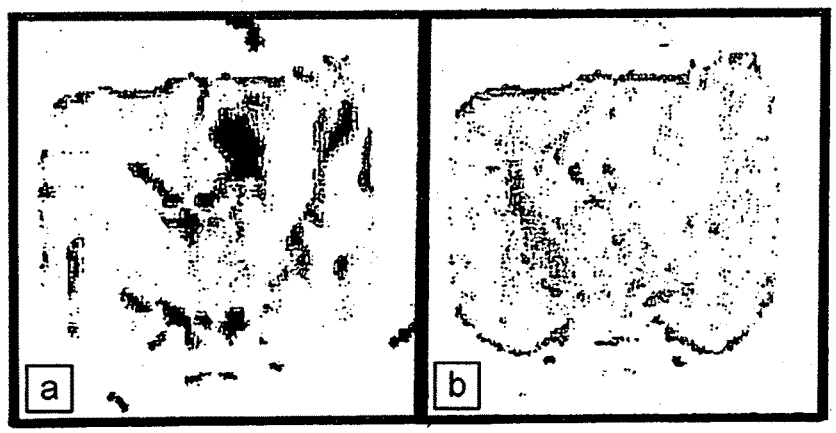

FIG. 8a is a computed diffusion tensor MR image revealing a map of the trace of the hydraulic conductivity tensor. Bright areas indicate regions of high conductivity.

FIG. 8b is an MR image demonstrating a map of the anisotropy of the hydraulic conductivity tensor. Bright areas indicate regions with high directionality (anisotropy) of the hydraulic conductivity.

Figure 9:
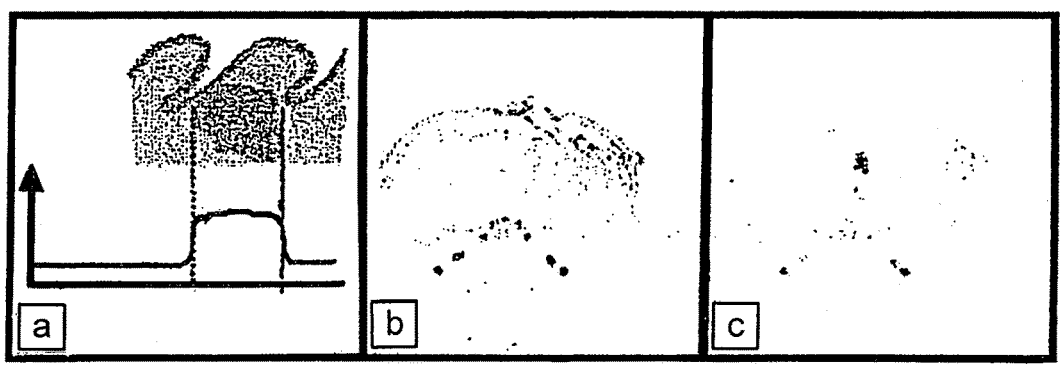

FIG. 9a is a schematic demonstrating the pressure differential between the extratumoral and the intratumoral interstitial pressures.

FIG. 9b is a contrast-enhanced $T_1$-weighted MR image showing a tumor in a dog brain. A catheter was placed through the tumor with the tip approximately 1 cm beyond the tumor mass, inside adjacent tissue.

FIG. 9c is a $T_1$-weighted MR image showing the same slice as that featured in panel b, with Gd-DTPA infused through the catheter. The image reveals that the fluid does not suffuse the tumor mass but rather distributes around one side of the catheter and the border of the tumor.

Figure 10:
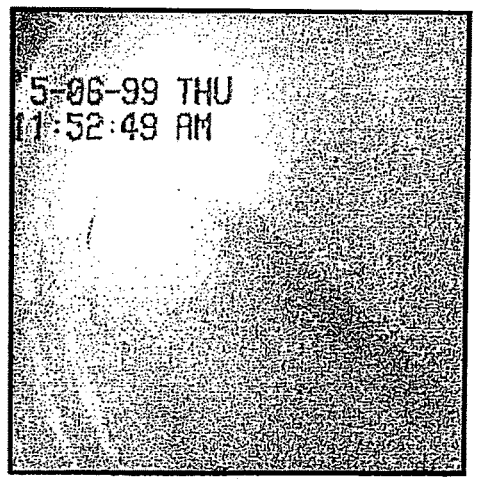

FIG. 10 is a digital camera shot depicting infusion of blue dye from an eight-port ventricular catheter inserted into an agarose gel preparation. Flow originated only from the most proximal port, rendering the remaining ports useless for drug delivery.

Figure 11:
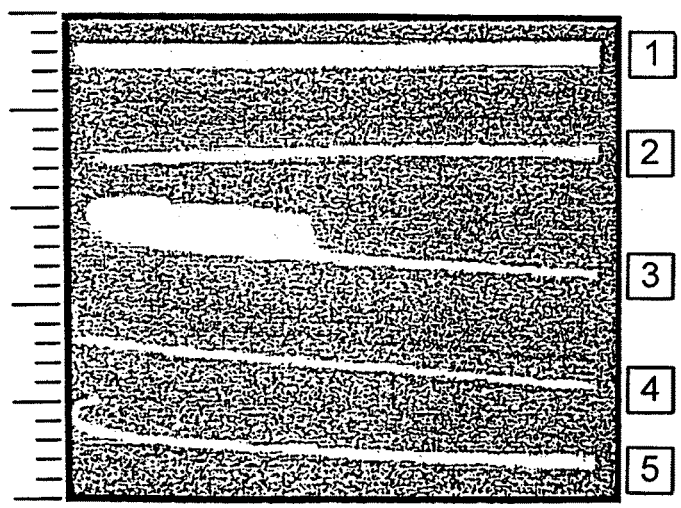

FIG. 11 is a photograph depicting the different types of catheters tested in the gel experiments. Scale on the left side of the image is 1 mm.

Figure 12:
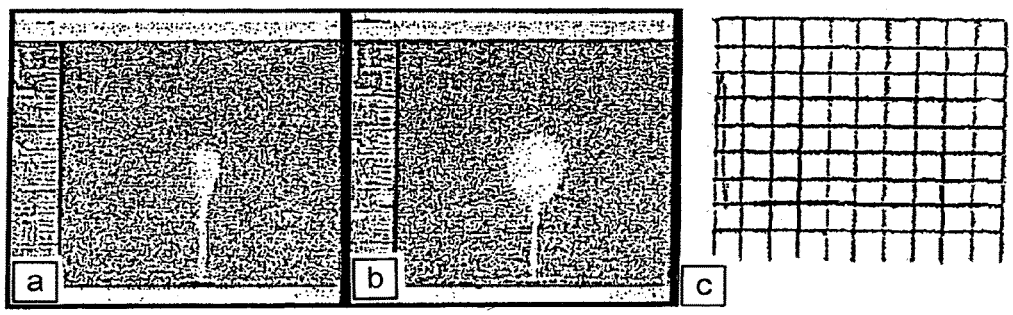

FIG. 12a is a digital camera shot depicting the volume of distribution for Catheter 1 at 10 minutes into infusion.

FIG. 12b is a digital camera shot depicting the volume of distribution for Catheter 1, 40 minutes into the infusion.

FIG. 12c is a graph of a pressure profile over time (pressure scale in mm Hg), showing a regular, slightly ellipsoid distribution, which is achieved due to the short backflow distance in conjunction with maintaining the structural integrity of the surrounding gel. The gel trial does not reveal issues that would limit the usability of the catheter for CED.

Figure 13:
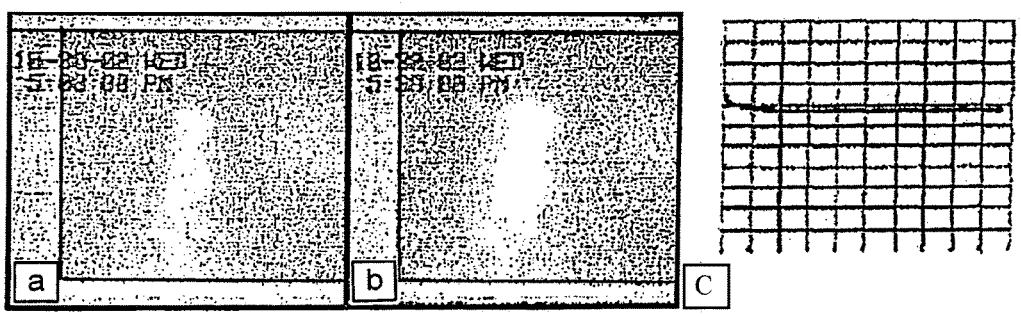

FIG. 13a is a digital camera shot depicting the volume of distribution for Catheter 2, 10 minutes into the infusion.

FIG. 13b is a digital camera shot revealing the volume of distribution for Catheter 2 at 40 minutes into the infusion.

FIG. 13c is a graph depicting a pressure profile over time (pressure scale in mm Hg), revealing a long backflow distance and a helical description of the gel structure, both indicating the limited suitability of this catheter for use in CED.

Figure 14:
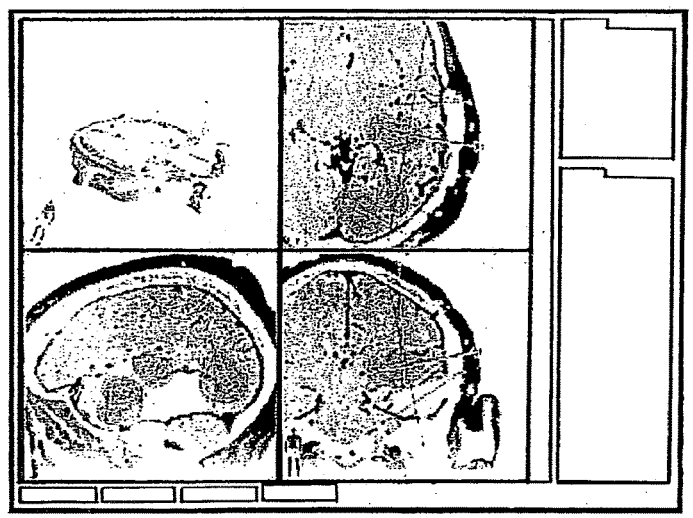

FIG. 14 is a screenshot of the iPlan! flow application (version 2) showing the planned trajectories for five catheters and the results of simulated infusion from these positions.

Figure 15B:
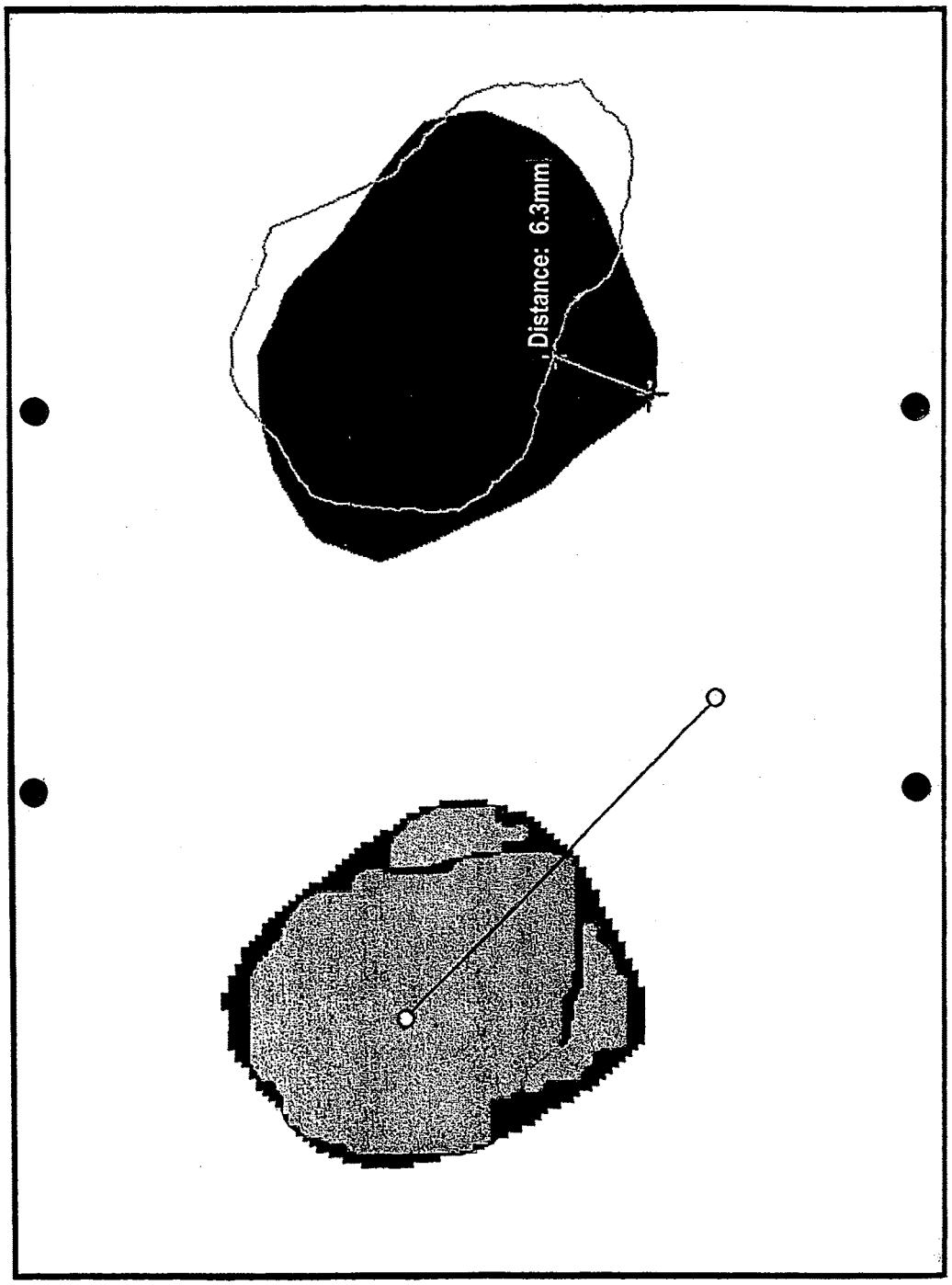

FIG. 15. A, Software dialogue box indicating a potentially poorly placed catheter trajectory at risk for failing to produce intraparenchymal distribution of the infusate. B, Volume of distribution ($V_d$) outlines for Catheter 3 in Patient 105 showing volume match between the SPECT and simulation. The $V_d$ of $^{123}$I-human serum albumin (HSA) measured by SPECT is shown in white. The orange area shows the area of overlap ($V_d$ match) between the simulation (SIM) and SPECT at the 50% isodose level. The green area shows the region where the SPECT Vd was larger than the simulation. The $V_d$ match between SPECT and simulation in this patient was 74%. C, Maximum in-plane deviation for Catheter 1 in Patient 106. The geometric distribution of $^{123}$I-HSA at the 50% isodose level as measured by SPECT is shown in white and is overlaid with result from the simulation (blue line). The maximum in-plane deviation which in this patient is 6.3 mm.

Figure 16:
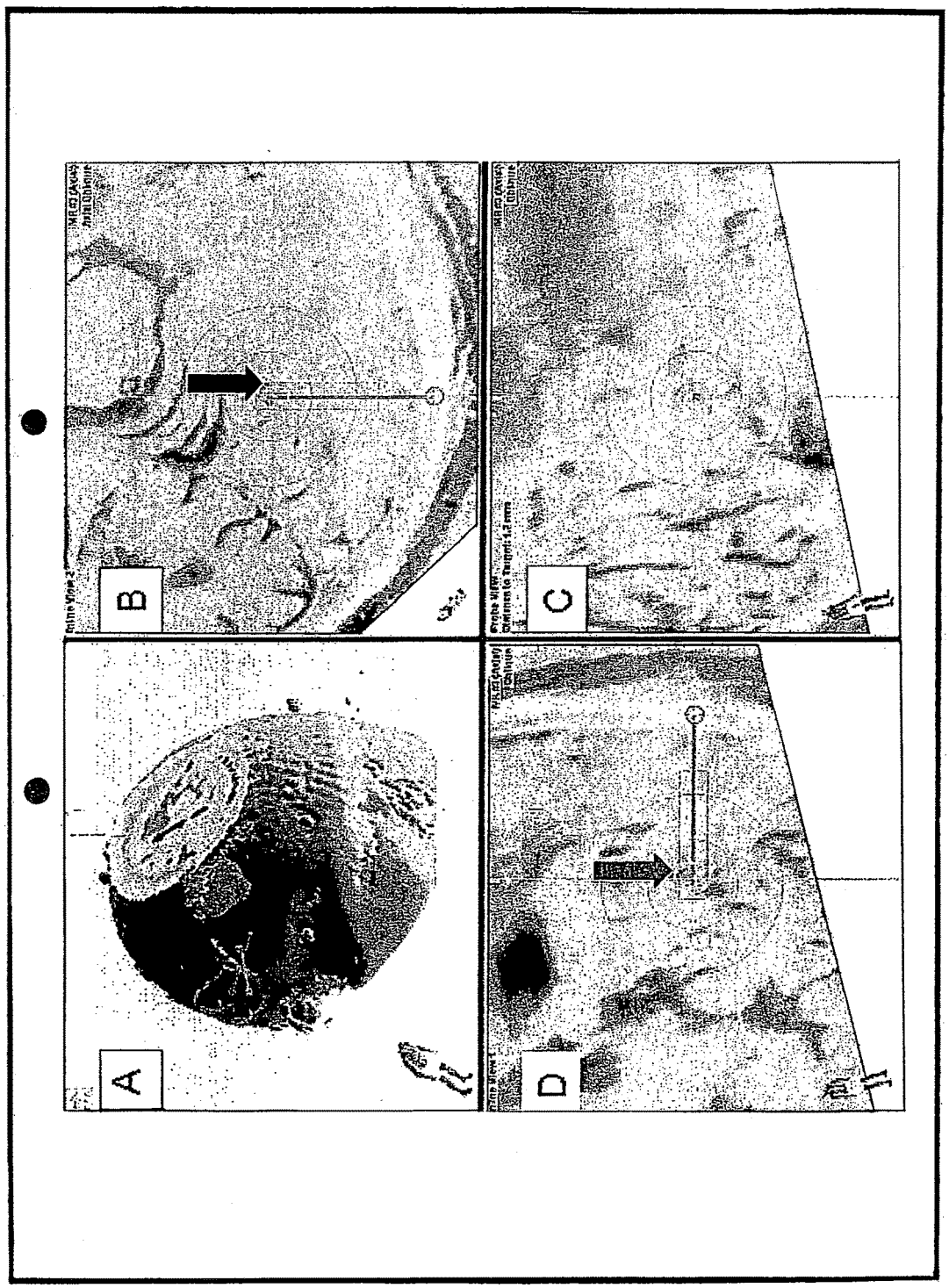

FIG. 16. T2-weight MR images showing catheter trajectory (green) in 3D reconstruction, two perpendicular cross sectional views, and an in-line view for Catheter 3 in Patient 108. The catheter crosses a sulcus 1.2 mm from its tip (yellow arrows).

Figure 17:
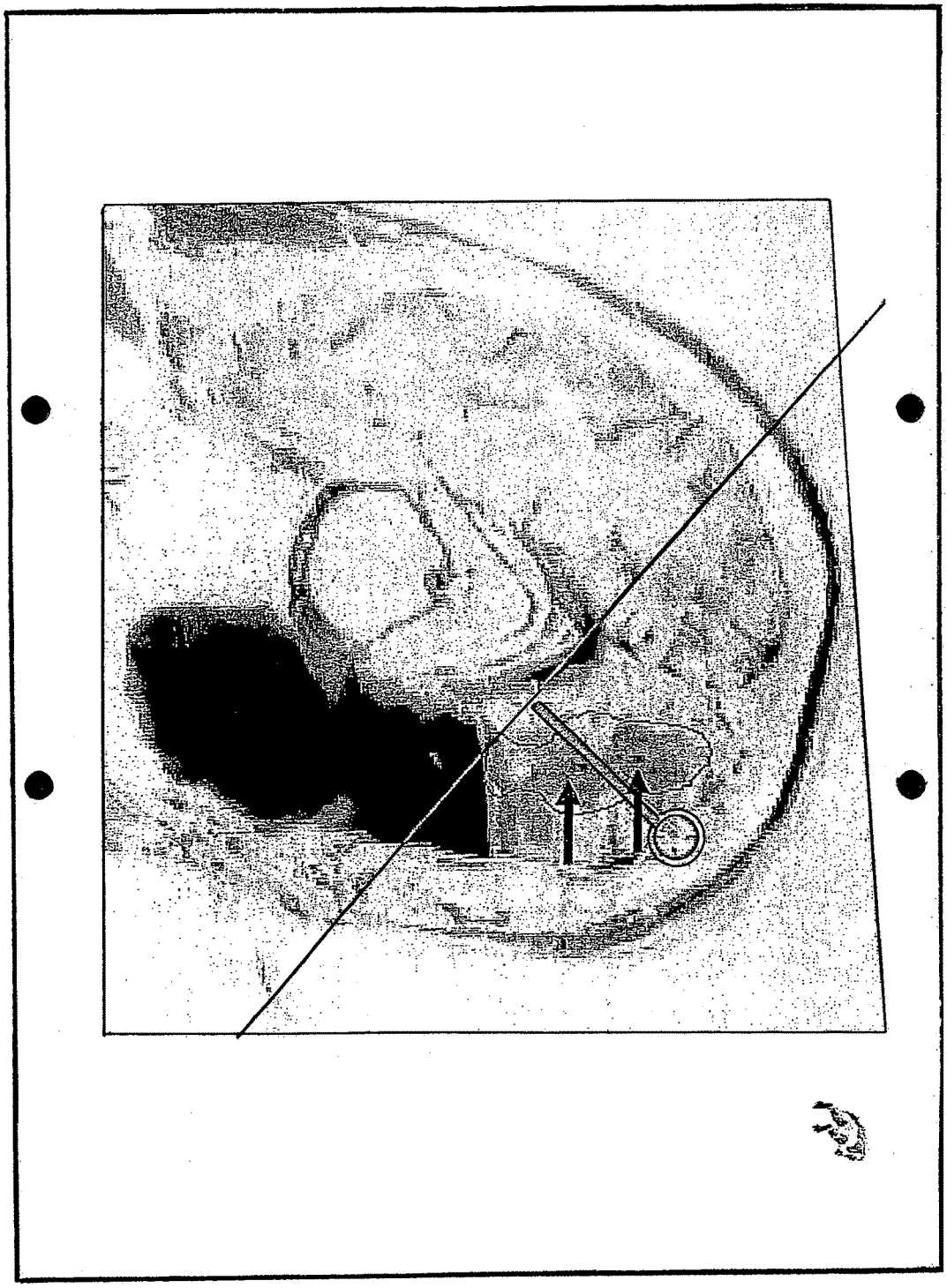

FIG. 17. T2-weighted MRI showing in-plane view of Catheter 1 in Patient 102. The catheter trajectory is shown in red. The image displays a thin linear hyperintensity (yellow arrows) corresponding to the trajectory of a previous catheter tract. The contour of the $^{123}$I-HSA distribution from the red catheter is shown at the 50% isodose level (yellow line).

Figure 18:
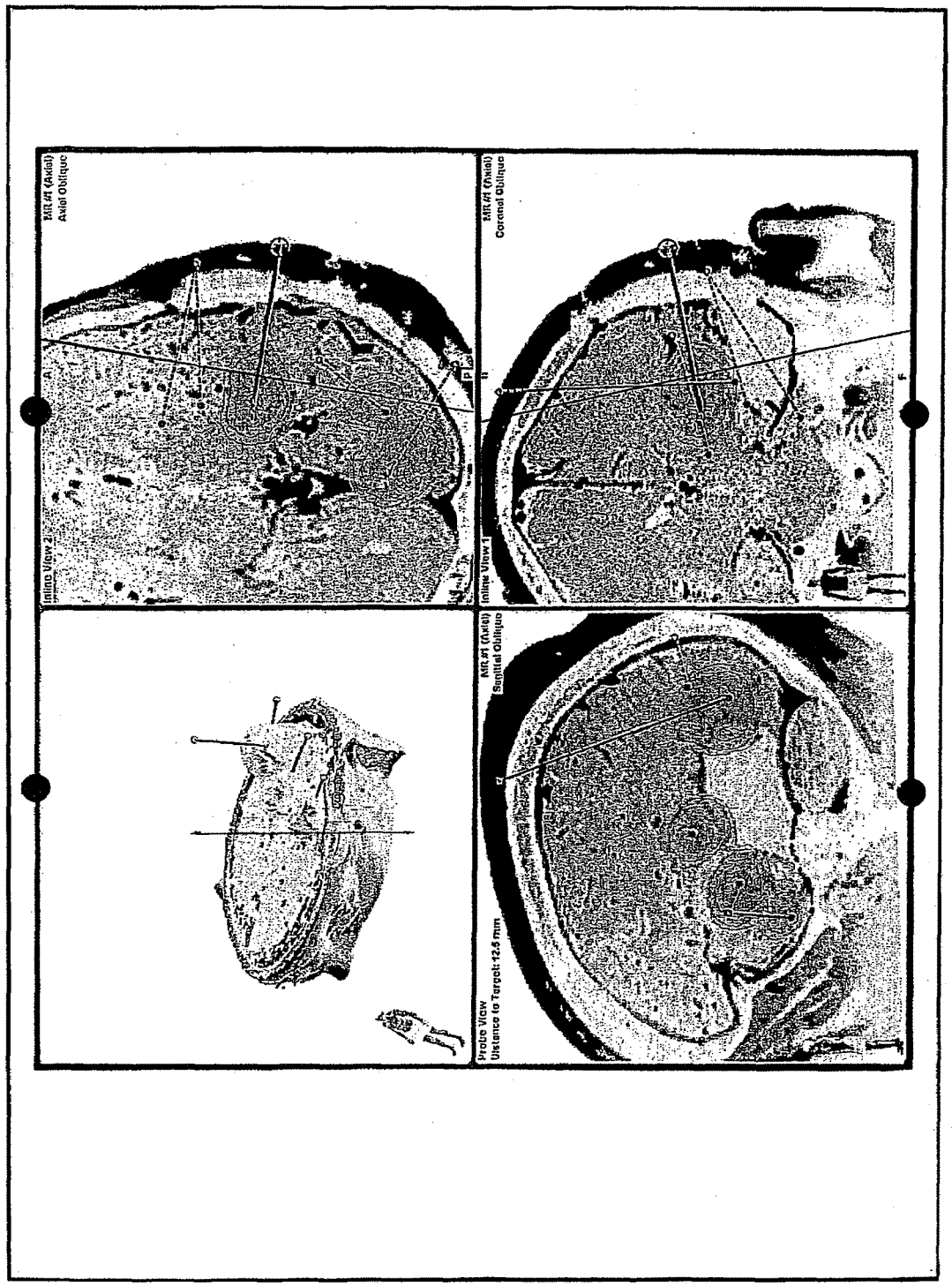

FIG. 18. T1-weighted MR images in various planes and 3D reconstruction showing "mock" distribution simulation. The distribution of the infusate at an effective concentration of 20% of the infused concentration is shown (blue shading) for 5 catheters (trajectories shown in yellow). Note that even 5 catheters in this patient would fail to provide an infusion volume that adequately covers the 2 cm margin surrounding this inferior temporal lobe resection cavity. The various contours represent the infusion at discrete time points (from inside out, 6, 12, 48, and 96 hours).

Figure 19:
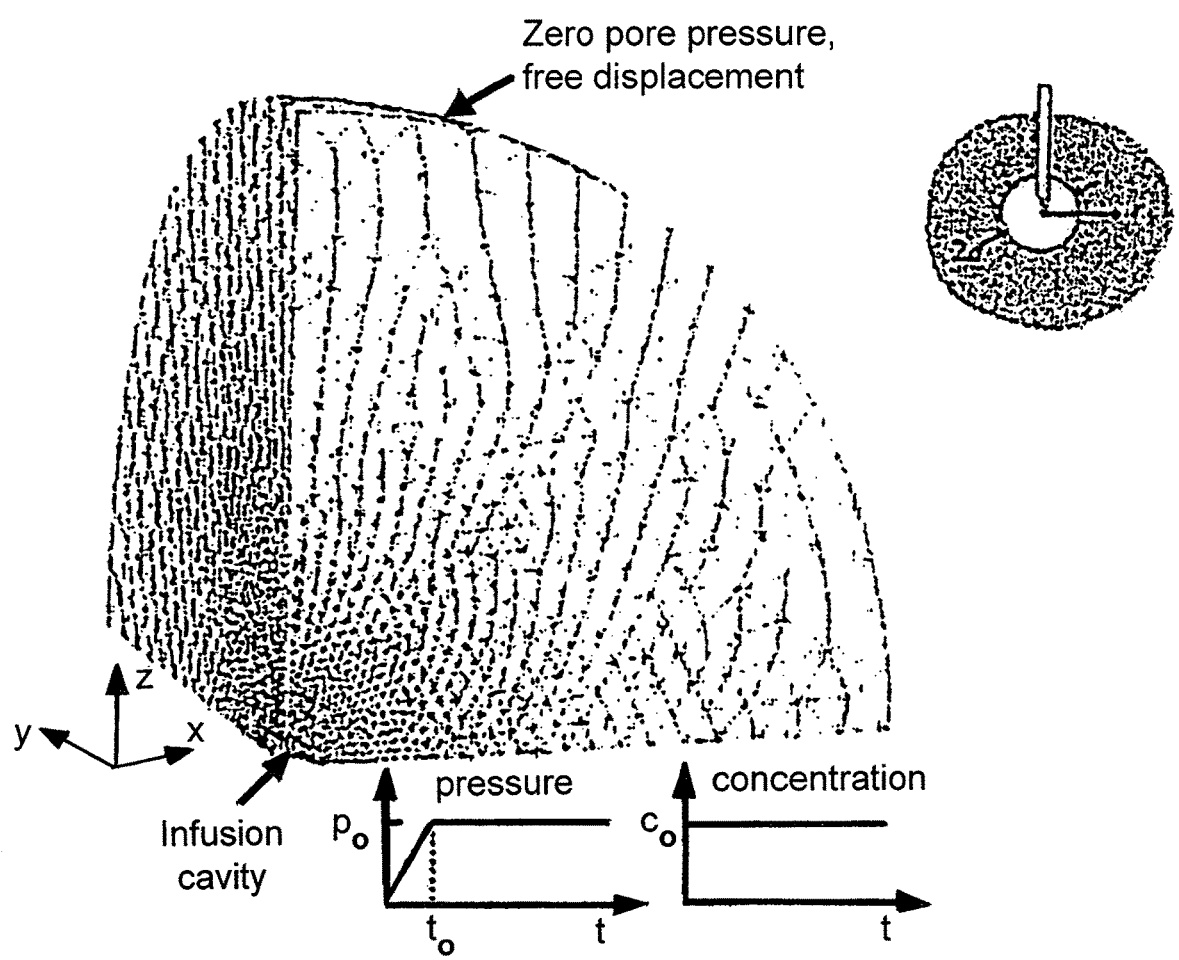

FIG. 19 is an FE mesh and boundary conditions used to model pressure-controlled infusion into tissue. The infusion cavity boundary conditions are applied at r=a ($a_0$=0.18 mm). The other radius of the tissue boundary is sufficiently distant that pore pressure is assumed negligible (r=20$a_0$).

Figure 20A:
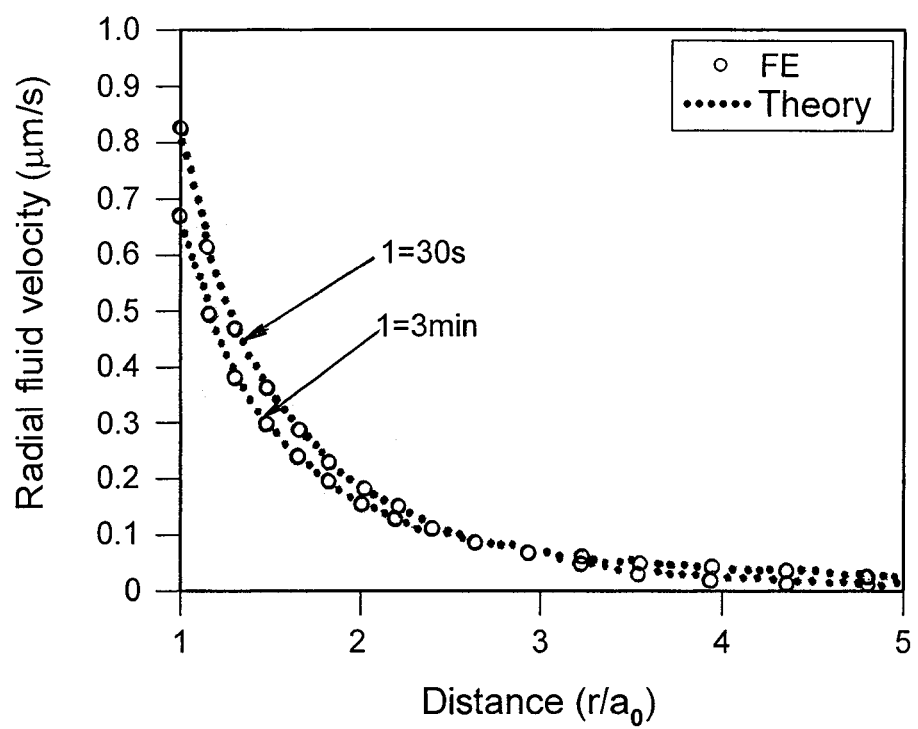
Figure 20B:
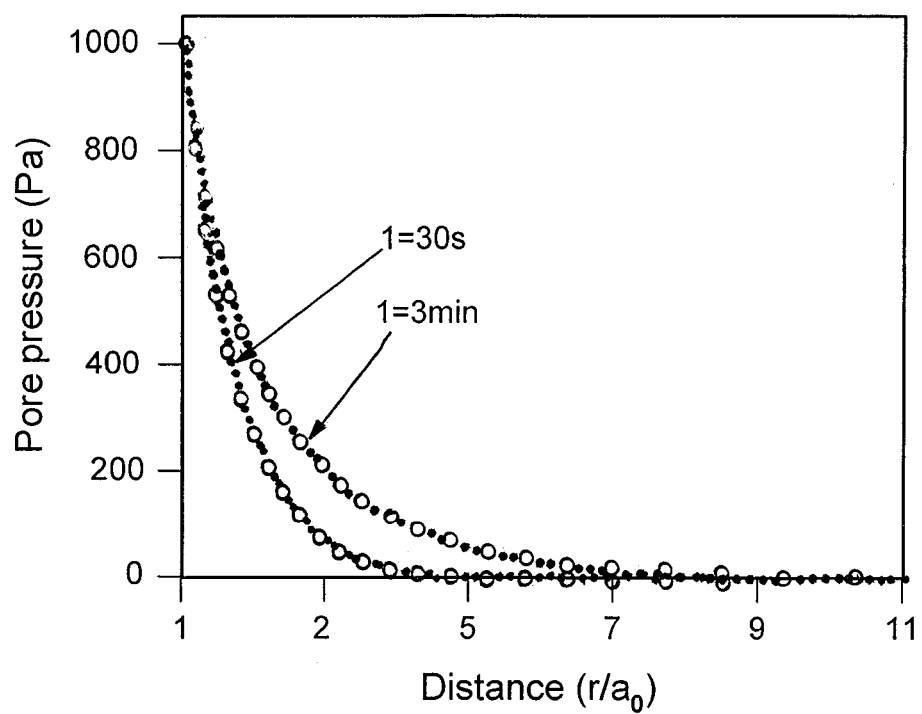
Figure 20C:
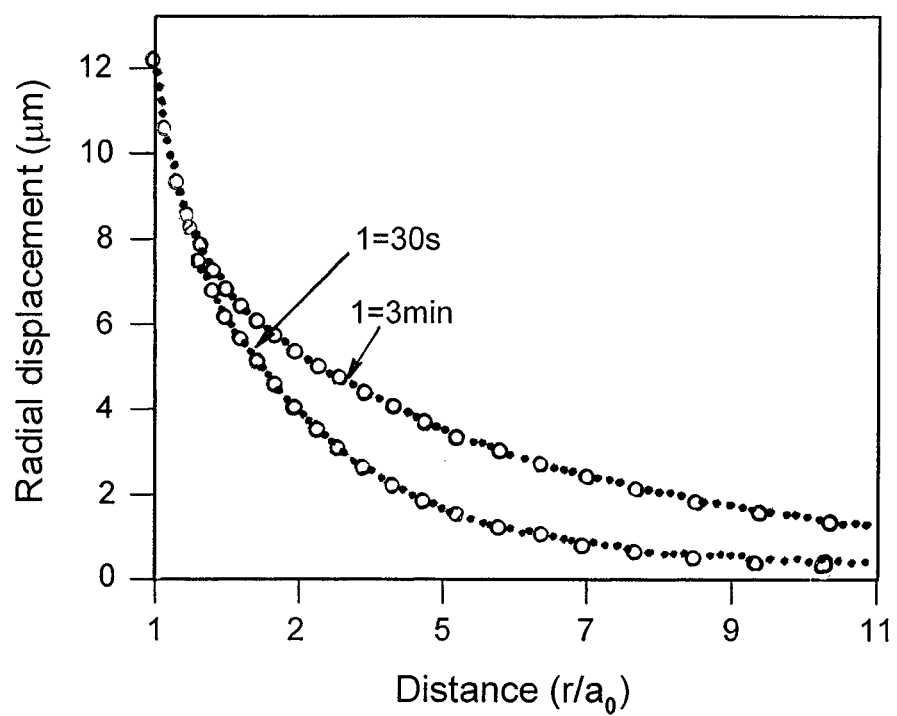
Figure 20D:
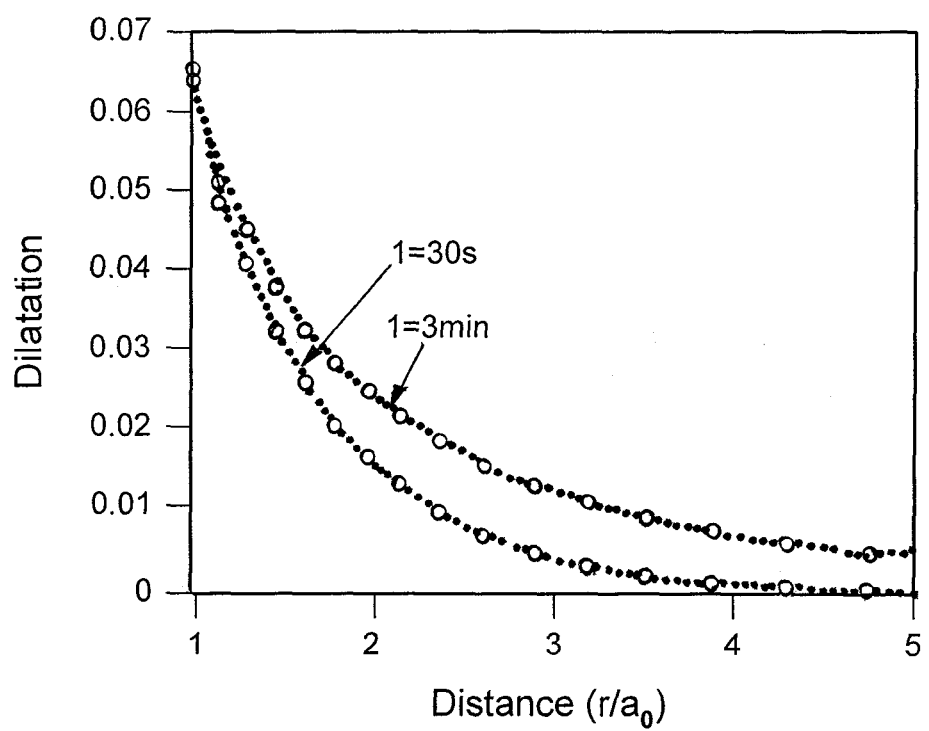

FIGS. 20a-20d are a validation analysis comparing transient FE and analytical solutions for infusion into tissue. FIG. 20a is a volume-averaged radial fluid velocity, $v_r = \varphi^f v^f$, FIG. 20b illustrates pore pressure, $\rho$; FIG. 20c illustrates radial displacement, $\mu$ and FIG. 20d illustrates dilation, e, with distance from the infusion cavity boundary. Model simulation parameters: E=10 kPa, $v$=0.35, $k_0$=1.0e-13 $m^4$ $N^{-1}$ $s^{-1}$, and $\rho_0$=1 kPa with instantaneous loading.

Reconstruction techniques follow the principle of stacking two-dimensional images on the top of each other to create a three-dimensional image. This is a common technique described among others in Linninger et al., Mimic Image Reconstruction for Computer-Assisted Brain Analysis, Mimic Innovation Awards 2005.

Positron emission tomography (PET) is a nuclear medicine imaging technique which produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis, often in modern scanners aided by results from a CT X-ray scan performed on the patient at the same time, in the same machine.

Single photon emission computed tomography (SPECT) is a nuclear medicine tomographic imaging technique using gamma rays. It is very similar to conventional nuclear medicine planar imaging using a gamma camera. However, it is able to provide true 3D information. This information is typically presented as cross-sectional slices through the patient, but can be freely reformatted or manipulated as required.

Darcy's law describes the flow of a fluid and is a simple proportional relationship between the instantaneous discharge rate through a porous medium, the viscosity of the fluid and the pressure drop over a given distance. Darcy's law is known since 1856.

The segmentation techniques such has region-growing-based methods is described among others in EP 1 768 062 A1 which teaching is included in this application. An example for such segmentation technique is: Segmenting method comprises preparing a reference data set assigned to a body structure image data set, determining the total imaging function which maps the reference data set onto the body structure image data set and defining limited body structures using the mapped reference data set in the body structure data set. Preferred Features: The total mapping function portion is determined by the decomposition of the body structure into structural parts and their individual new arrangement in front of the other total mapping function portion.

Further, the method to calculate the volume for an infusion fluid is described in Morrison papers, Linninger paper (Linninger et al., Mimic Image Reconstruction for Computer-Assisted Brain Analysis, Mimic Innovation Awards 2005), Chen paper (Annals of Biomedical Engineering, 2007) and Raghavan paper (Neurosurg, Focus 20, 2006). An example for such method is described in U.S. Pat. No. 6,549,803 and is summarized as follows:

Movement of material in an organism, such as a drug injected into a brain, is modelled by a uniformly structured field of static constants governing transport by moving fluid and diffusion within the fluid. This supports planning of material introduction, (e.g., infusion, perfusion, retroperfusion, injections, etc.) to achieve a desired distribution of the material, continuing real-time feedback as to whether imaged material is moving as planned and will be distributed as desired, and real-time plan modification to improve results.

A further example for such method is described below in Chen paper (Annals of Biomedical Engineering, 2007):

Methods

Mechanics Model

A brief description of the biphasic theory used in the model is presented. For a more expanded description, the reader is referred to Mow et al. Nervous tissue was treated as a mixture, which includes a solid phase (label: s) and a fluid phase (label: f). Both solid and fluid phases were assumed to be incompressible with the solid matrix fully saturated with fluid. The fluid phase included the infusate which was assumed to have the same fluid properties as the interstitial fluid. Low solute concentrations were assumed, and the influence of the solute on fluid flow and tissue deformation was considered negligible. Also, osmotic effects were not considered.

The constitutive equations for solid and fluid phases are $$\sigma^s = -\phi^s pI + \sigma^E (\sigma^E = \lambda eI + 2\mu\varepsilon) \quad (1)$$

$$\sigma^f = -\phi^f pI \quad (2)$$

where $\sigma^s$ and $\sigma^f$ are the Cauchy stress tensors of the solid and fluid phases; $\sigma^E$ is the contact stress from deformation of the solid matrix; $\varphi^s$ and $\varphi^f$ are the solid and fluid volume fractions ($\varphi^s + \varphi^f = 1$); $\varepsilon$ is the infinitesimal strain tensor of the solid matrix ($\varepsilon = \frac{1}{2}[\nabla u + \nabla u^T]$ where u is the displacement vector); e is the dilatation $e = Tr(\varepsilon)$; $\lambda$ and $\mu$ are the Lamé elastic constants of the solid matrix; p is the pore (interstitial) fluid pressure; and I is the identity tensor.

Fluid flow is described by Darcy's law as $$-k\nabla p = v - v^s \quad (3)$$

where $v = \varphi^s v^s + \varphi^f v^f$ is the volume-averaged bulk velocity; $v^s$ and $v^f$ are the velocity vectors of solid and fluid phases; and k is the hydraulic permeability. Hydraulic permeability has been found to be deformation-dependent due to localized changes in porosity for soft tissues such as cartilage and hydrogels. For small deformation, Lai and Mow proposed an exponential relationship $$k = k_0 \exp(Me) \quad (4)$$

where M is a material constant and $k_0$ is the baseline hydraulic permeability at zero strain (no deformation). The spatially varying porosity, $\varphi^f$, due to solid deformation is related to the initial porosity, $\varphi^f_{02}$, and the Jacobian, $J = dV/dV_0$, by $\varphi^f = 1 - (1-\varphi^f_0)/J$. For small deformation $J = 1+e$, and the porosity is calculated by $$\phi^f = \frac{e + \phi_0^f}{1+e}. \quad (5)$$

The conservation of mass for tissue is given by $$\nabla \cdot v = q^f \quad (6)$$

where $q^f$ is the source term for the fluid phase. We assumed no fluid source term for the fluid phase. Absorption of fluid by capillaries was assumed to be negligible, and there are no lymphatics in nervous tissue. In addition, although there exists slow cerebro-spinal fluid (CSF) circulation within the brain, which arises out of the continuous bulk flow of CSF from the choroids plexus formation sites to the arachnoid villi absorptions sites, this bulk flow was considered negligible compared with induced flow due to infusion. Taking divergence on both sides of Eq. (3) and applying Eq. (6) results in $$\nabla \cdot (k\nabla p) = \frac{\partial e}{\partial t} + q^f \quad (7)$$

where $q^f = -\beta(\partial p/\partial t)$ in the FE formulation (see below). Neglecting inertia and body force terms, the balance of momentum for the solid-fluid mixture requires $$\nabla \cdot (\sigma^s + \sigma^f) = \nabla \cdot (-pI + \sigma^E) = 0 \quad (8)$$

The nature of the coupled solid-fluid interaction can be further illustrated by rewriting Eq. (8) using $e = \nabla u$ and taking divergence on both sides $$(\lambda + 2\mu)\nabla^2 e = \nabla^2 p \quad (9)$$

Assuming initial conditions, $p(x, t) = e(x, t) = 0$ at $t = 0$, results in $$p = H_A \cdot e (H_A = \lambda + 2\mu) \quad (10)$$

and Eq. (7) can be written as $$\nabla \cdot (\bar{k} H_A \nabla e) = \frac{\partial e}{\partial t}\left(\bar{k} = \frac{k}{1+\beta H_A}\right) \quad (11)$$

which is similar in form to equations of heat conduction or diffusion. The FE formulation assumed $\beta$=constant, even though no fluid source term was assumed. Hydraulic permeability of the tissue, k, was related to input hydraulic permeability, k, using Eq. (11).

Solute Transport Model

Mass conservation for the solute in tissue is given by $$\frac{\partial M_c c}{\partial t} + \nabla \cdot (M_c c v^c) = q^c \quad (12)$$

where c is the solute concentration in mole per unit volume of the whole mixture; $M_c$ is the molecular weight of the solute; $v^c$ is the velocity of solute; and $q^c$ is the source term for the solute. We consider solute transport that is confined to the fluid and solute phases only (extracellular). Transport behavior is described by Fick's law $$c(v^c - \bar{v}) = -D_{eff} \nabla c \quad (13)$$

where $D_{eff}$ is the effective diffusion tensor of the solute in the porous media.

$$\bar{v} = \frac{1}{\rho} \sum_{\alpha=f,c} \rho^\alpha v^\alpha$$

is the density-averaged velocity of the fluid and solute mixture, $\rho^\alpha$ is the apparent density of constituent $\alpha$, and $\rho=\Sigma_{\alpha=f,c}\rho^\alpha$. We assumed the solute concentration was too low to influence the density of the mixture and the velocity of the fluid. Thus, $\bar{v}$ can be approximated by $v^f$. In addition, the solid matrix-solute interaction will hinder the convection transport, which is corrected by including a retardation coefficient, $\chi$. Thus, $\bar{v}=\chi\ v^f$. Substituting Eq. (13) into Eq. (12) results in the relation $$\frac{\partial c}{\partial t} + \nabla \cdot (c \chi v^f - D_{eff} \cdot \nabla c) = \frac{q^c}{M_c} \qquad (14)$$

Volumetric extravasation, absorption, and degradation of the tracer solute were assumed negligible ($q^c=0$) during direct infusion. In addition, $\chi$ and $D_{eff}$ are affected by the porosity which changes with tissue deformation. In this study, unless otherwise mentioned, $\chi=1$, and $D_{eff}$ was assumed to be independent of tissue deformation. Changes in diffusional transport may be small compared to the overall distribution if interstitial transport is dominated by convection.

Numerical Implementation

The computational model was developed using the FE software package ADINA (version 8.2.2, ADINA R&D Inc., Watertown, Mass.) along with user-defined subroutines and a custom C++ program. Three modules were used to solve for solid deformation, fluid flow, and solute transport equations (denoted by ADINA-S, ADINA-T, and ADINA-F, respectively). The coupled solid deformation and fluid flow equations (Eqs. 7 and 8 expressed in terms of u and p) were solved using ADINA-S and ADINA-T modules simultaneously. The Newton-Raphson iteration method was used to solve FE-discretized equations, and an Euler-backward integration scheme was used for the transient solutions. u and p solutions were obtained at each time point. Note that solutions were obtained assuming $\beta$=constant and related to the case $\beta$=0 using the hydraulic permeability relation defined by Eq. (11).

The quasi-static biphasic solution was incorporated in the solute transport problem (Eq. 14) using the ADINA-F module. The biphasic-solute transport solution interface was achieved using a custom C++ program which: (1) calculated the nodal dilatation, porosity, and fluid velocity at each time step; and (2) created and compiled the model for solute transport computation using the fluid velocity field at that time step. Nodal deformation velocity was calculated by dividing the displacement difference between two neighboring time steps with the time step, $v_1^s=(u_t-u_{t-\Delta t})/\Delta t$. $v^f$ was calculated using the relations $v=\phi^s v^s+\phi^f v^f$ and Eq (5). Since fluid velocity was output at the integration point, nodal fluid velocity was then approximated by averaging the fluid velocities at the surrounding integration points.

Tissue Infusion Model

We considered solute infusion into gray matter which was idealized as a homogeneous, isotropic, biphasic media with no fluid source or sink regions and negligible endogenous interstitial fluid flow. A symmetric, spherical geometry was modeled and the infusion site was a spherical cavity with radius, $\alpha$. The initial radius of the infusion cavity corresponded to the external diameter of a 28-gauge cannula, $\alpha_0$=0.18 mm. The outer radius was 20 $\alpha_0$=3.6 mm. Previous infusion analyses show that pore pressure, displacement, and fluid velocity change negligibly at radial positions more than 20$\alpha_0$ away. A FE mesh was created using 4-node tetrahedral elements (~42,000 elements) with finer meshing in the region close to the infusion site (FIG. 19). Zero initial pore pressure, strain, and fluid flow were assumed.

Pressure within the infusion cavity was assumed uniform, and a ramp-hold pressure was applied at the spherical boundary. Solid, fluid, and solute transport boundary conditions were applied separately. Previous studies by Kenyon and Hou et al. used a zero contact stress ($\sigma^E=0$) applied to the solid phase at the interface between fluid and porous media. Since the stress calculated in the solid module of ADINA-S was the total stress for the bulk material ($\sigma^s+\sigma^f$), the infusion pressure was applied at the porous media-fluid interface at r=$\alpha$, i.e., the infusion cavity surface, which moves during infusion. Also, a constant solute concentration boundary condition was applied on this surface. Zero pore pressure and free displacement were applied along the outer tissue boundary. Symmetric boundary conditions were applied to symmetry faces (zero displacement, flow flux, and mass flux normal to the surface). Infusion parameters were varied, and sensitivity to changes in infusion pressure, $\rho_0$, over the range 1-10 kPa (7.5-75 mmHg), was determined. Infusion pressure is likely on the lower end of this range based on experiments of Prabhu et al., who observed a range of infusion pressures in the rat caudate of 1.6-4.2 kPa (12-32 mmHg) for infusion rates varying between 0.17 and 1.5 μL/min (25-gauge needle). The lower pressure value is also in the vicinity of the consolidated tissue pressure (~2.4 kPa) measured after an hour of infusion at 0.5 μL/min into the white matter of the corona radiata of cats. The time to reach constant pressure, $I_0$ to, was considered of short duration.

The influence of material parameters on pressure-induced tissue swelling and solute transport was considered. In addition, biphasic and solute transport solutions were compared with rigid model solutions. Table 4 lists the range of parameters used in this study. The value of Young's modulus of the solid matrix was set to range from 1 to 10 kPa. This range corresponds well with modulus values estimated for small strains tested under low strain rate conditions by Miller and Chinzei, E~1 kPa The range of Poisson ratio has been previously estimated by Mostachfi et al. to range between 0.3 and 0.4, based on literature values and the compliant behavior of brain tissues.

Very few experimental studies have attempted to measure the hydraulic permeability of nervous tissue. The baseline hydraulic permeability for the gray matter was chosen between 1.0e-13 and 1.0e-12 $m^4N^{-1}\ s^{-1}$. This range was established from the spread of dye through the brain following cold-induced edema by Reulen et al. and the estimated ranges of previous poroelastic brain models. A deformation-dependent hydraulic permeability was also considered and we used the exponential relation by Lai and Mow. The value for the material constant M was varied between 0 and 5 based on a previous range established for cartilage and hydrogels. Porosity was varied between 0.2 and 0.3. The lower range of porosity corresponds to measures by radiotracer methods and iontophoretic measurements of tetramethyl-ammonium ($TMA^+$) in non-infused tissues. The lower porosity values also match the volume ratio, $V_{infusion}/V_{distribution}$, of CED striatum distribution studies of $^{14}C$-albumin by Chen et al. The upper porosity range is characteristic of values reported elsewhere for edematous states, which occur after prolonged infusion or local damage to tissue. Diffusivity of the solute in gray matter was set to correspond to the macromolecular tracer albumin, MW-66 kDa. The apparent diffusion coefficient of fluorescently labeled bovine serum albumin has been measured by Tao and Nicholson in rat cortical slices using an integrative optical imaging system, $D_{eff}$=1.6e-11 m$^2$/s.

TABLE 4

Material parameter ranges of gray matter brain tissue used in simulation studies.

| Parameter | Range |
| --- | --- |
| Young's modulus, E | 1-10 kPa |
| Poisson ratio, ν | 0.3-0.4 |
| Baseline hydraulic permeability, $k_0$ | $10^{-13}$-$10^{-12}$ m$^4$N$^{-1}$s$^{-1}$ |
| Nonlinear parameter, M | 0-5 |
| Porosity, $\varphi^\dagger$ | 0.2-0.3 |
| Diffusivity (albumin), $D_{eff}$ | $1.6 \times 10^{-11}$ m$^2$/s |

The FE biphasic solution was validated by comparing with previous analytical solutions by Basser for infusion into an infinite biphasic media with constant hydraulic permeability. Solutions for pore pressure and fluid velocity following a step change in pressure infusion ($t_0$=0) were compared (Rather than instantaneously applied pressure, simulations ramp infusion pressure rapidly with a ramp time 0.02 s). FIG. 20 illustrates a validation analysis comparing transient FE and analytical solutions for infusion into tissue. FIG. 20*a* is a volume-averaged radial fluid velocity, $v_r = \varphi^f v^f$, FIG. 20*b* illustrates pore pressure, ρ; FIG. 20*c* illustrates radial displacement, μ and FIG. 20*d* illustrates dilation, e, with distance from the infusion cavity boundary. Model simulation parameters: E=10 kPa, ν=0.35, $k_0$=1.0e-13 m N$^{-1}$ s$^{-1}$, and $\rho_0$=1 kPa with instantaneous loading. Also, an analytical solution of displacement was solved and compared to the FE solution.

The invention claimed is:

1. A method of operating a medical planning and navigation system comprising an imaging device, a computer including a processor and a non-transient memory, and a human viewable display for planning an infusion of a fluid drug, the method comprising:

using the processor of the computer, identifying one or more target regions in a tissue for local delivery of the fluid drug, said identifying comprising:
i) obtaining, via the imaging system, at least one of functional anatomical image data, structural anatomical image data, or functional and structural anatomical image data corresponding to at least one of an edema, a resection cavity, or an edema and a resection cavity, wherein the at least one of the functional anatomical image data, the structural anatomical image data, or the functional and structural anatomical image data comprises at least one of magnetic resonance (MR) derived data, single photon emission computed tomography (SPECT) derived data, position emission tomography (PET) derived data, or ultrasound or computed tomography (CT) derived data, the at least one of the functional anatomical image data, the structural anatomical image data, or the functional and structural anatomical image data being evaluated by image processing techniques two-dimensionally with respect to distribution information contained in the at least one of the functional anatomical image data, the structural anatomical image data, or the functional and structural anatomical image data; and
ii) using the processor of the computer, evaluating the at least one of the functional anatomical image data, the structural anatomical image data, or the functional and structural anatomical image data, said evaluating comprising using segmentation techniques to determine at least one of:
a margin around the resection cavity,
a volume of the edema, or
a volume of the edema and a margin around the resection cavity,
the determined at least one of the margin around the resection cavity, the volume of the edema, or the volume of the edema and the margin around the resection cavity being the identified one or more target regions for the local delivery of the fluid drug;
using the processor of the computer, obtaining, from the at least one of the functional anatomical image data, the structural anatomical image data, or the functional and structural anatomical image data, a rate of change of a concentration of the fluid drug based on an anisotropic diffusion tensor of a molecule of the fluid drug;
using the processor of the computer, computing a pressure profile along an associated delivery device used for the local delivery of the fluid drug, the pressure profile being computed based on a poroelastic model of backflow such that backflow of the fluid drug along an insertion track of the associated delivery device is minimized; and
using the computed pressure profile as a boundary condition for obtaining by the processor of the computer a planned interstitial pressure of the fluid drug to be delivered to the one or more target regions of the tissue.

2. The method as set forth in claim 1, wherein the evaluating the at least one of the functional anatomical image data, the structural anatomical image data, or the functional and structural anatomical image data comprises:
evaluating the at least one of the functional anatomical image data, the structural anatomical image data, or the functional and structural anatomical image data by one or more image processing techniques three-dimensionally with respect to distribution information contained in the at least one of the functional anatomical image data, the structural anatomical image data, or the functional and structural anatomical image data.

3. The method as set forth in claim 1, wherein the evaluating the at least one of the functional anatomical image data, the structural anatomical image data, or the functional and structural anatomical image data comprises:
evaluating the at least one of the functional anatomical image data, the structural anatomical image data, or the functional and structural anatomical image data by one or more image processing techniques over a period of time with respect to distribution information contained in the at least one of the functional anatomical image data, the structural anatomical data, or the functional and structural anatomical image data; and
making an adjustment in the distribution information to at least one of anatomical or structural conditions which have changed over the period of time.

4. The method as set forth in claim 1, further comprising determining a diffusion velocity of the fluid drug using Diffusion Weighted-derived Images in combination with the at least one of the MR derived data, the SPECT derived data, the PET derived data, or the Ultrasound or CT derived data.

5. The method as set forth in claim 1, further comprising determining the isotropy of flow directions in at least one of the one or more target regions or surrounding tissue by analyzing Diffusion Tensor data in combination with the at least one of the MR derived data, the SPECT derived data, the PET derived data, or the Ultrasound or CT derived data.

6. The method as set forth in claim 1, further comprising: calculating a distribution volume for the fluid drug by one or more segmentation techniques from the at least one of the functional anatomical image data, the structural anatomical image data.

7. The method as set forth in claim 1, further comprising determining the at least one of the functional anatomical image data, the structural anatomical image data, or the functional and structural anatomical image data three-dimensionally using one or more segmentation techniques.

8. The method according to claim 1, wherein the identifying the one or more target regions in the tissue comprises identifying one or more target regions of brain tissue, and the method further comprising planning a location for the infusion using medical navigation.

9. The method as set forth in claim 1, further comprising determining the at least one of the functional anatomical image data, the structural anatomical image data, or the functional and structural anatomical image data two-dimensionally by one or more segmentation techniques.

10. The method as set forth in claim 9, further comprising combining a number of two dimensional data sets on the at least one of the functional anatomical image data, the structural anatomical image data, or the functional and structural anatomical image data using one or more reconstruction techniques to obtain three-dimensional information.

11. The method according to claim 1, wherein the identifying the one or more target regions in the tissue comprises identifying one or more target regions of brain tissue, and the method further comprising planning an introduction of an infusion device at a selected point using stereotactic planning.

12. The method as set forth in claim 11, further comprising combining the at least one of the functional anatomical image data, the structural anatomical image data, or the functional and structural anatomical image data with information in an expected distribution of the fluid drug for planning at least one of infusion treatment or navigation.

13. The method according to claim 12, wherein the combining the information comprises overlaying at least one of:
   anatomical tissue data,
   functional tissue data,
   structural tissue data or
   functional and structural tissue data
with an expected infusion distribution of the fluid drug.

14. A device for planning an infusion of a fluid drug, the device comprising:
   an imaging device configured to image associated tissue and capture at least one of functional anatomical image data, structural anatomical image data, or functional and anatomical image data;
   a computer configured to, based on the captured functional anatomical image data, the anatomical image data, or the functional and structural anatomical image data, perform at least one of:
      i) evaluate the at least one of the functional anatomical image data, the structural anatomical image data, or the functional and structural anatomical image data to identify in the associated tissue at least one of advantageous or non-advantageous infusion regions of a fluid drug, wherein the at least one of the functional anatomical image data, the structural anatomical image data, or the functional and anatomical image data comprises at least one of magnetic resonance (MR) derived data, single photon emission computed tomography (SPECT) derived data, position emission tomography (PET) derived data, or ultrasound or computed tomography (CT) derived data, the at least one of the functional anatomical image data, the structural anatomical image data, or the functional and anatomical image data being evaluated by image processing techniques two-dimensionally with respect to distribution information contained in the at least one of the functional anatomical image data, the structural anatomical image data, or the functional and anatomical image data, or
      ii) produce and evaluate a distribution simulation of the fluid drug, the distribution simulation simulating the fluid drug being introduced at particular points relative to the associated tissue; and
   a computer-assisted medical planning and navigation system for assisting in positioning an associated infusion device to deliver the fluid drug to one or more target regions, the medical planning and navigation system being configured to assist in the positioning by:
      identifying the one or more target regions in the associated tissue for local delivery of the fluid drug, said identifying comprising:
         i) obtaining from the imaging device the at least one of the functional anatomical image data, the structural anatomical image data, or the functional and anatomical image data corresponding to at least one of an edema, a resection cavity, or an edema and a resection cavity; and
         ii) evaluating the at least one of the functional anatomical image data, the structural anatomical image data, or the functional and anatomical image data corresponding to the at least one of the edema, the resection cavity, or the edema and resection cavity, said evaluating comprising using segmentation techniques to determine at least one of:
            a margin around the resection cavity,
            a volume of the edema, or
            a volume of the edema and a margin around the resection cavity,
         the at least one of the margin around the resection cavity, the volume of the edema, or the volume of the edema and the margin around the resection cavity being the one or more target regions for the local delivery of the fluid drug;
      obtaining, from the at least one of the functional anatomical image data, the structural anatomical image data, or the functional and anatomical image data, a rate of change of a concentration of the fluid drug based on an anisotropic diffusion tensor of a molecule of the fluid drug;
      computing a pressure profile along the associated infusion device used for the local delivery of the fluid drug, the pressure profile being computed based on a poroelastic model of backflow such that backflow of the fluid drug along an insertion track of the associated infusion device is minimized; and
      using the computed pressure profile as a boundary condition for obtaining a planned interstitial pressure of the fluid drug to be delivered to the one or more target regions of the tissue.

15. The device as set forth in claim 14, wherein the imaging device, the computer, and the medical planning and navigation system are operatively connected with each other via data connections for a constant retrievable exchange of data.

16. The method according to claim 1, wherein the using the one or more segmentation techniques comprises using one or more region-growing-based methods.

\* \* \* \* \*